(12) United States Patent
Harrison et al.

(10) Patent No.: US 9,931,356 B2
(45) Date of Patent: *Apr. 3, 2018

(54) PHARMACOKINETICS OF S-ADENOSYLMETHIONINE FORMULATIONS

(71) Applicant: METHYLATION SCIENCES INTERNATIONAL SRL, Christchurch (BB)

(72) Inventors: Nancy Harrison, North Vancouver (CA); I. David MacDonald, Surrey (CA); Aniko Takacs-Cox, North Vancouver (CA); Robert Miller, Delta (CA)

(73) Assignee: METHYLATION SCIENCES INTERNATIONAL SRL, Worthing, Christ Church (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/245,105

(22) Filed: Aug. 23, 2016

(65) Prior Publication Data

US 2016/0361339 A1 Dec. 15, 2016

Related U.S. Application Data

(60) Continuation of application No. 14/472,204, filed on Aug. 28, 2014, now abandoned, which is a continuation of application No. 13/706,188, filed on Dec. 5, 2012, now Pat. No. 8,865,203, which is a division of application No. 12/845,600, filed on Jul. 28, 2010, now Pat. No. 8,329,208.

(60) Provisional application No. 61/229,186, filed on Jul. 28, 2009.

(51) Int. Cl.
| | |
|---|---|
| A61K 47/00 | (2006.01) |
| A61K 9/00 | (2006.01) |
| A61K 31/70 | (2006.01) |
| A61K 31/7076 | (2006.01) |
| A61K 9/20 | (2006.01) |
| A61K 9/28 | (2006.01) |
| A61K 47/38 | (2006.01) |
| A61K 9/50 | (2006.01) |

(52) U.S. Cl.
CPC ........ *A61K 31/7076* (2013.01); *A61K 9/0002* (2013.01); *A61K 9/0053* (2013.01); *A61K 9/2054* (2013.01); *A61K 9/2095* (2013.01); *A61K 9/28* (2013.01); *A61K 9/2886* (2013.01); *A61K 9/50* (2013.01); *A61K 47/38* (2013.01)

(58) Field of Classification Search
None
See application file for complete search history.

(56) References Cited

U.S. PATENT DOCUMENTS

| | | |
|---|---|---|
| 3,893,999 A | 7/1975 | Fiecchi |
| 3,954,726 A | 5/1976 | Fiecchi |
| 4,057,686 A | 11/1977 | Fiecchi |
| 4,389,393 A | 6/1983 | Schor et al. |
| 4,525,345 A | 6/1985 | Dunn et al. |
| 4,537,772 A | 8/1985 | Alexander et al. |
| 4,556,678 A | 12/1985 | Hsiao |
| 4,601,894 A | 7/1986 | Hanna et al. |
| 4,680,323 A | 7/1987 | Lowey |
| 4,687,757 A | 8/1987 | Parrott et al. |
| 4,692,337 A | 9/1987 | Ukigaya et al. |
| 4,695,591 A | 9/1987 | Hanna et al. |
| 4,756,911 A | 7/1988 | Drost et al. |
| 4,968,509 A | 11/1990 | Radebaugh et al. |
| 5,073,380 A | 12/1991 | Babu et al. |
| 5,128,249 A | 7/1992 | Gennari |
| 5,137,712 A | 8/1992 | Kask et al. |
| 5,169,642 A | 12/1992 | Brinker et al. |
| 5,264,446 A | 11/1993 | Hegasy et al. |
| 5,439,687 A | 8/1995 | Compassi |
| 5,462,747 A | 10/1995 | Radebaugh et al. |
| 5,543,154 A | 8/1996 | Rork et al. |
| 5,753,213 A | 5/1998 | Moratti |
| 5,922,341 A | 7/1999 | Smith et al. |
| 6,004,575 A | 12/1999 | Luessen et al. |

(Continued)

FOREIGN PATENT DOCUMENTS

| | | |
|---|---|---|
| CA | 2298245 A1 | 8/2000 |
| CN | 101677543 A | 3/2010 |

(Continued)

OTHER PUBLICATIONS

Baldrick, "Pharmaceutical Excipient Development: The Need for Preclinical Guidance," Regul Toxicol Pharmacology 32(2):210-218 (2000).

Bottiglieri et al., "Ademetionine (S-adenosylomethionine) neuropharmacology: implications for drug therapies in psychiatric and neurological disorders," Exp Opin Invest Drugs 6(4):417-426 (1997).

Bottiglieri et al., "Transmethylation in depression," Alabama J Med Sci 25(3):296-301 (1988).

European Patent Application No. 10803973.6 Communication dated Jul. 27, 2015.

(Continued)

*Primary Examiner* — Jessica Worsham
(74) *Attorney, Agent, or Firm* — Wilson Sonsini Goodrich & Rosati

(57) ABSTRACT

Compositions and methods to improve the pharmacokinetic profile of S-Adenosylmethionine (SAMe) are provided, as are methods of treating various disorders using SAMe formulations with improved pharmacokinetic profiles. More specifically, the invention is directed to methods of treating a disease or disorder in a subject and/or improving the nutritional status of a subject by administering formulations exhibiting improved pharmacokinetic profiles of exogenous SAMe. The method also includes the step of orally administering compositions of the invention to the subject once per day after overnight fast; that is prior to food intake in the morning.

15 Claims, 10 Drawing Sheets

(56) References Cited

U.S. PATENT DOCUMENTS

| | | | |
|---|---|---|---|
| 6,093,703 | A | 7/2000 | La Greca |
| 6,548,555 | B1 | 4/2003 | Curatolo et al. |
| 6,555,124 | B1 | 4/2003 | Kolter et al. |
| 6,596,701 | B1 | 7/2003 | Schwartz et al. |
| 6,759,395 | B2 | 7/2004 | Rao et al. |
| 6,943,155 | B2 | 9/2005 | Lichtenberger |
| 8,329,208 | B2 | 12/2012 | Harrison et al. |
| 8,580,296 | B2 | 11/2013 | Harrison et al. |
| 8,865,203 | B2 | 10/2014 | Harrison et al. |
| 2002/0106345 | A1 | 8/2002 | Uhrich et al. |
| 2002/0164369 | A1 | 11/2002 | Rao et al. |
| 2004/0028729 | A1 | 2/2004 | Shojaei et al. |
| 2005/0142187 | A1 | 6/2005 | Treacy et al. |
| 2005/0158382 | A1 | 7/2005 | Cruz et al. |
| 2005/0171034 | A1 | 8/2005 | Halevie-Goldman |
| 2005/0191349 | A1 | 9/2005 | Boehm et al. |
| 2005/0267023 | A1 | 12/2005 | Sinclair et al. |
| 2006/0013905 | A1 | 1/2006 | Tehoharides et al. |
| 2006/0094782 | A9 | 5/2006 | Wong et al. |
| 2006/0127506 | A1 | 6/2006 | Hebert |
| 2006/0130160 | A1 | 6/2006 | Dumas et al. |
| 2006/0280789 | A1 | 12/2006 | Ueki et al. |
| 2007/0196272 | A1 | 8/2007 | Eddington et al. |
| 2007/0196501 | A1 | 8/2007 | Paterson et al. |
| 2008/0206333 | A1 | 8/2008 | Freedman |
| 2008/0279931 | A1 | 11/2008 | Morrow |
| 2009/0088404 | A1 | 4/2009 | Freedman et al. |
| 2009/0110729 | A1 | 4/2009 | Giovannone et al. |
| 2009/0197824 | A1 | 8/2009 | Freedman et al. |
| 2011/0027342 | A1 | 2/2011 | MacDonald et al. |
| 2011/0027360 | A1 | 2/2011 | Harrison et al. |
| 2013/0129792 | A1 | 5/2013 | Harrison et al. |
| 2013/0142847 | A1 | 6/2013 | MacDonald et al. |
| 2013/0149350 | A1 | 6/2013 | Harrison et al. |
| 2014/0370108 | A1 | 12/2014 | Harrison et al. |

FOREIGN PATENT DOCUMENTS

| | | |
|---|---|---|
| DE | 19839443 A1 | 3/2000 |
| DE | 102005024614 A1 | 11/2006 |
| EP | 1731596 A1 | 12/2006 |
| EP | 2149369 A1 | 2/2010 |
| EP | 2464358 A2 | 6/2012 |
| JP | S6072815 A | 4/1985 |
| JP | 2002504514 A | 2/2002 |
| JP | 2003155242 A | 5/2003 |
| JP | 2005320354 A | 11/2005 |
| JP | 2007508248 A | 4/2007 |
| JP | 2008163009 A | 7/2008 |
| WO | WO-0112155 A1 | 2/2001 |
| WO | WO-0249637 A1 | 6/2002 |
| WO | WO-02083136 A1 | 10/2002 |
| WO | WO-02092112 A1 | 11/2002 |
| WO | WO-2005034920 A1 | 4/2005 |
| WO | WO-2006044202 A2 | 4/2006 |
| WO | WO-2006079212 A1 | 8/2006 |
| WO | WO-2007095092 A2 | 8/2007 |
| WO | WO-2008065502 A1 | 6/2008 |
| WO | WO-2008095142 A1 | 8/2008 |
| WO | WO-2010027014 A1 | 3/2010 |
| WO | WO-2010063756 A1 | 6/2010 |
| WO | WO-2011012990 A2 | 2/2011 |

OTHER PUBLICATIONS

Giulidori et al., "Pharmacokinetics of S-adenosyl-L-methionine in healthy volunteers," Eur J Clin Pharmacol 27:119-121 (1984).
Gren and Nystrom, "Porous cellulose matrices containing lipophilic release modifiers—a potential oral extended-release system," Intl. J. Pharmaceutics 184:7-19 (1999).
He et al., "Determination and pharmacokinetics of S-adenosylmethionine in human plasma by solid-phase extraction—LC-MS," J China Pharmaceutical University 40(1):67-71, 2009 (with English translation).
Eudragit L 100. http://eudragitevonik.com/product/eudragit/en/products-services/eudragit-products/enteric-formulations/1-100/Pages/default.aspx as referenced on Aug. 25, 2012, 2 pages.
Eudragit S 100. http://eudragit.evonik.com/product/eudragit/en/products-services/eudragit-products/enteric-formulations/s-100/Pages/default.aspx as referenced on Aug. 25, 2012, 2 pages.
Kaye et al., "Metabolism of Exogenous S-Adenosyl-L-Methionine in Patients with Liver Disease," Drugs 40:124-128 (1990).
Luo et al., "S-adenosylmethionine inhibits the growth of cancer cells by reversing the hypomethylation status of c-myc and H-ras in human gasatric cancer and colon cancer," (2010) Int. J. of Biological Sciences; Dec. 6; 6(7); 784-795.
McMillan et al., "S-adenosyl-L-methionine: transcellular transport and uptake by Caco-2 cells and hepatocytes," Journal of Pharmacy and Pharmacology (2005) 57:599-605.
PCT/CA2011/050462 International Preliminary Report on Patentability dated Jan. 29, 2013.
PCT/CA2011/050462 Search Report dated Aug. 15, 2011.
PCT/CA2011/050462 Written Opinion dated Sep. 23, 2011.
PCT/IB2010/001877 International Preliminary Report on Patentability dated Feb. 9, 2012.
PCT/IB2010/001877 Search Report and Written Opinion dated Dec. 9, 2010.
PCT/IB2010/001879 International Preliminary Report on Patentability dated Feb. 9, 2012.
PCT/IB2010/001879 Search Report and Written Opinion dated Mar. 21, 2011.
PCT/US08/52726 International Preliminary Report on Patentability dated Dec. 30, 2008.
PCT/US08/52726 Search Report dated May 21, 2008.
PCT/US08/52726 Written Opinion dated May 21, 2008.
PCT/US09/36703 International Preliminary Report on Patentability dated Jan. 18, 2011.
PCT/US09/36703 Search Report dated Jan. 13, 2010.
PCT/US09/36703 Written Opinion dated Jan. 13, 2010.
PCT/US09/51076 International Preliminary Report on Patentability dated Jan. 18, 2011.
PCT/US09/51076 Search Report dated Feb. 17, 2010.
PCT/US09/51076 Written Opinion dated Feb. 17, 2010.
Sahelian, "SAM-e" Datasheet [online] [retrieved on Aug. 15, 2011 from internet archive dated Jul. 3, 2004], 3 pages. <original URL:http://www.raysahelian.com/sam-e.html>.
Stramentinoli et al., Intestinal absorption of S-Adenosyl-L-Methionine. The Journal of Pharmacology and Experimental Therapeutics, 209(3):323-326 (1979).
Stramentinoli et al., "Pharmacologic aspects of S-adenosylmethionine-Pharmacokinetics and pharmacodynamics," Am J Med 83(5):35-42 (1987).
U.S. Appl. No. 12/182,036 Final Office Action dated Dec. 30, 2013.
U.S. Appl. No. 12/182,036 Office Action dated Feb. 23, 2012.
U.S. Appl. No. 12/182,036 Office Action dated Mar. 15, 2013.
U.S. Appl. No. 12/845,555 Office Action dated Jun. 5, 2014.
U.S. Appl. No. 12/845,555 Office Action dated Nov. 8, 2011.
U.S. Appl. No. 12/845,555 Office Action dated Oct. 8, 2013.
U.S. Appl. No. 13/706,188 Office Action dated Jun. 5, 2014.
U.S. Appl. No. 13/706,188 Office Action dated Oct. 9, 2013.
U.S. Appl. No. 13/811,772 Office Action dated Aug. 9, 2016.
U.S. Appl. No. 13/811,772 Office Action dated Jan. 14, 2016.
U.S. Appl. No. 13/811,772 Office Action dated Jan. 29, 2014.
U.S. Appl. No. 13/811,772 Office Action dated Aug. 13, 2015.
U.S. Appl. No. 14/472,204 Office Action dated Feb. 23, 2016.
U.S. Appl. No. 12/845,555 Final Office Action dated Aug. 29, 2012.
U.S. Appl. No. 12/845,600 Final Office Action dated Aug. 21, 2012.
U.S. Appl. No. 12/845,600 Office Action dated Nov. 8, 2011.
U.S. Appl. No. 13/714,246 Non-Final Office Action dated Apr. 24, 2013.
U.S. Appl. No. 13/811,772 Office Action dated Nov. 19, 2014.
Whitehead, et al., Safe and Effective Permeation Enhancers for Oral Drug Delivery. Pharm. Res. 25 (8), 2008, 1783-1788.
www.merriam-webster.com/dictionary/food [retrieved from the internet]. Referenced on Nov. 4, 2011 [retrieved on May 5, 2012]. 4 pages.

(56) References Cited

OTHER PUBLICATIONS

Yang et al., "Pharmacokinetic properties of S-denosylmethionine after oral and intravenous administration of its tosylate disulfate salt: A multiple-dose, open-;label, parallel-group study in healthy Chinese volunteers," Clin. Therapeutics 31(2):311-320 (2009).

Stramentinoli et al, Adomet as a drug. Pharmacokinetic and Pharmacological Aspects. In: Biological Methylation and Drug Design, R.T. Borchardt, New Jersey, Humana Press: p. 315-326 (1986).

US 9,931,356 B2

PHARMACOKINETICS OF S-ADENOSYLMETHIONINE FORMULATIONS

CROSS-REFERENCE TO RELATED APPLICATIONS AND CLAIM TO PRIORITY

This application claims priority to U.S. Provisional patent application Ser. No. 61/229,186, filed Jul. 28, 2009, which is incorporated herein by reference in its entirety.

TECHNICAL FIELD

The invention relates to compositions and methods for improving the pharmacokinetic profile of S-adenosyl-L-methionine ("SAM-e" or "SAMe"). More particularly, the invention concerns formulations that lead to SAMe plasma concentrations and AUC values that are increased in comparison to similar or higher doses of conventional SAMe formulations. The invention is directed to methods of treating a disease or disorder in a subject and/or improving the nutritional status of a subject by administering formulations exhibiting improved pharmacokinetic profiles of exogenous SAMe. The method also includes orally administering compositions of the invention to the subject once per day after overnight fast, that is prior to food intake in the morning, which may alleviate some of the side effects (e.g. insomnia and gastrointestinal) associated with conventional twice-daily (or more) dosing regimens. Compositions of the invention may also provide a faster rate of onset of exogenous SAMe in comparison to conventional oral dosage forms potentially leading to improvements in efficacy.

BACKGROUND OF THE INVENTION

S-adenosyl-L-methionine ("SAMe") is a naturally occurring compound that is present in tissues throughout the body. At the molecular level, SAMe is involved in various metabolic pathways, including transmethylation, transsulfuration and aminopropylation.

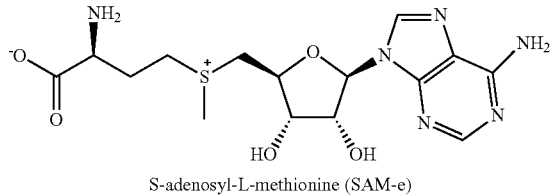

S-adenosyl-L-methionine (SAM-e)

In the body, SAMe is synthesized from an amino acid, methionine, and a triphosphate nucleotide, ATP. SAMe has been tested in numerous clinical trials for the treatment of various ailments, including arthritis, liver disease and depression.

SAMe supplementation was initially considered impractical, due to the instability of the SAMe ion during manufacturing, shipping and storage. Eventually stable salts of SAMe were developed (such as SAMe tosylate disulfate, the butanedisulfonate salt of SAMe, the di-para-toluene sulfonate disulfate of SAMe, the tri-para-toluene sulfonic acid salt of SAMe and the like). These salts can be formulated using standard, known technologies used for non-parenteral administration including but not limited to tablets, capsules and pellets. Formulations such as these may also comprise a coating which can serve multiple purposes such as reducing stomach irritation, improving taste and ease of swallowing, as well as stabilizing the encapsulated SAMe from elements such as moisture. Stable salts of SAMe are described in, for example, U.S. Pat. Nos. 3,954,726 and 4,057,686, both of which are incorporated herein by reference in their entirety. Conventional SAMe API is supplied as a molecular entity comprising an ion along with several counter-ions. For example, SAMe ion plus a tosylate and 2 sulfonic acid counter-ions make up commercially available adenosylmethionine disulfate-p-toluenesulfonate (also referred to as SAMe tosylate disulfate). When referring to SAMe dosing, it is currently accepted in the art that the numerical dose (usually in milligrams) refers to the amount of SAMe ion which is administered. For example, reference to a "400 mg SAMe tablet" of the SAMe tosylate disulfate would include the 400 mg of SAMe ion, another 370 mg of the counter-ions, and 200-300 mg of additional excipient to make up a final tablet weight of 1.0-1.1 grams. Thus, for example, a 1600 mg oral dose of SAMe which is generally reported in the art would typically be a dose of four such 1.0-1.1 gram tablets taken at one time. Alternatively, the same 1600 mg dose of SAMe ion may also be accomplished by administration of other combinations of multiple tablets such as, sixteen 100 mg or eight 200 mg tablets of SAMe ion taken at a given time. Conventional oral dosage forms of SAMe are most commonly produced with about 400 mg of SAMe ion; above that, the larger dosage form becomes difficult for swallowing considering that even at 400 mg of SAMe ion the tablets are quite large at 1.0-1.1 grams.

Exogenous SAMe exposure may be measured by looking at multiple pharmacokinetic parameters, the most common being the $C_{max}$, $T_{max}$ and AUC. After non-parenteral administration of SAMe, its concentration in the blood increases until it reaches a peak concentration, this measured in plasma is the $C_{max}$, and the time taken to reach the $C_{max}$ is termed, $T_{max}$. The area under the (plasma concentration) curve, or AUC, is another useful measurement and represents the drug exposure in the systemic circulation over a period of time.

A few studies examining these pharmacokinetic parameters in humans have been recorded for SAMe. The role of intravenous (IV) versus oral administration of SAMe has been investigated to a small extent as well as the effect of repeat dosing over time. Giulidori et al., report plasma drug levels and half-lives of SAMe after a single, IV administered dose (Giulidori, P. et al., (1984) *Eur. J. Clin. Pharmacol.* 27:119.) Another group looked at SAMe plasma levels after a single, orally administered dose (Stramentinoli, G. (1987) *Am. J. Med.* 83:35.) A recent study examines SAMe pharmacokinetic parameters after one-day and five-day doses of orally and IV administered SAMe tosylate disulfate (Yang, J. et al (2009) *Clin. Therapeutics*, 31 (2): 311.) The prior art indicates that the half-life of oral SAMe is short and that AUC values of oral formulations are low.

There exists a need in the art to generate non-parenteral SAMe formulations with improved pharmacokinetic profiles compared to conventional prior art SAMe dosage forms. For example, those which have increased $C_{max}$ and/or AUC values as well as those which are more potent and exhibit similar $C_{max}$ and AUC values at low doses of SAMe. High $C_{max}$ or AUC formulations may produce an increased biological response to SAMe supplementation and 'high potency' formulations would have the benefit of a lower pill count and potentially increased tolerability for desired $C_{max}$ and/or AUC values.

SUMMARY OF THE INVENTION

The present inventors have discovered that the pharmacokinetic (PK) profile of exogenous SAMe can be significantly improved by designing dosage forms to release substantial amounts of SAMe within a particular "window" of dissolution. Formulations that release the vast majority of SAMe extremely early (i.e. those exhibiting an initial "burst" of drug) and those that are slower in their drug release are unable to achieve improved in vivo PK profiles of SAMe. The investigators here identify compositions and methods that are designed to release SAMe within this unexpected "window" of preferred drug release levels. Thus, in some exemplified embodiments, compositions that exhibit improved SAMe PK profiles have targeted amounts of drug release within a defined dissolution "window"—this in vitro correlates to a specified time interval for preferred drug release and in vivo relates to transition through a specific region of the gastrointestinal tract.

In some embodiments of the invention improved in vivo PK profiles are generated when combining exogenous SAMe with suitable excipients and/or processing parameters that impart specific product characteristics such as, for example, thickness, water content, friability, hardness, disintegration or dissolution properties. Accordingly, exemplified embodiments of the present invention relate to non-parenteral compositions and methods which exhibit improved pharmacokinetic profiles, specifically high in vivo SAMe $C_{max}$ values and/or increased AUC values, in comparison to conventional prior art SAMe dosage forms. In some exemplified embodiments, provided are improved PK SAMe compositions which exhibit a targeted amount of drug release over a desired range of locations within the gastrointestinal tract of a fasted individual. In certain embodiments, targeted drug release is achieved by use of one or more functional coatings such that the functional coating allows for extensive dissolution of the composition at the precise time interval in vitro. In some embodiments, targeted drug release formulations are identified in vitro using low pH dissolution profiles. Low pH dissolution studies are performed at below the standard of pH 6.8. Accordingly, the invention also provides an in vitro screening method which utilizes specific dissolution profiles of formulation candidates to identify products which yield improved pharmacokinetic values in vivo. Standard dissolution methods do not effectively distinguish these improved PK formulations from others. Obtaining dissolution profiles at low pH values (mimicking the pH of a specific location within the duodenum or upper small intestine where the formulations of the invention are targeted to release) in comparison to dissolution profiles at pH 6.8 (which best represents the pH of the distal small intestine) identifies rapid, yet targeted, dissolution formulations as leading to improved pharmacokinetic parameters in vivo.

In other exemplified embodiments, compositions which exhibit improved SAMe PK profiles are generated under conditions of very low relative humidity. It is generally known that SAMe should be manufactured under conditions of low humidity (less than about 35%) in order to make products of workable consistency. However, the investigators here have found that SAMe formulations generated when humidity is maintained at very low conditions, below about 10%, exhibit additional benefits such as improved PK profiles which are less affected by variations in additional parameters such as coating thickness.

There is provided herein a composition comprising a physiologically effective dosage of SAMe, wherein non-parenteral administration of said composition to a selected subject group produces in said selected subject group an effect comprising one of: a. an average maximum SAMe blood plasma concentration (average $C_{max}$) of at least about 1800 ng/mL for a 1600 mg dosage of SAMe ion; b. an average SAMe plasma area under the curve (average AUC) of at least about 7500 ng·h/mL for a 1600 mg dosage of SAMe ion; or, c. an average maximum SAMe blood plasma concentration (average $C_{max}$) of at least about 850 ng/mL and/or an average SAMe plasma area under the curve (average AUC) of at least about 4000 ng·h/mL for a 800 mg dosage of SAMe ion; or, d. an average maximum SAMe blood plasma concentration (average Cmax) of at least about 400 ng/mL and/or an average SAMe plasma area under curve (average AUC) of at least about 1800 ng·h/mL for a 400 mg dosage of SAMe ion; or, e. an average maximum SAMe blood plasma concentration (average Cmax) of at least about 200 ng/mL and/or an average SAMe plasma area under curve (average AUC) of at least about 900 ng·h/mL for a 200 mg dosage of SAMe ion; or, f. an average maximum SAMe blood plasma concentration (average Cmax) of at least about 100 ng/mL and/or an average SAMe plasma area under curve (average AUC) of at least about 450 ng·h/mL for a 100 mg dosage of SAMe ion. In some embodiments, the composition comprises physical or chemical dosage form characteristics which modulate one of said average SAMe $C_{max}$ and said average SAMe AUC. In some embodiments, the composition is in a dosage form manufactured at a relative humidity of less than 10%. In some embodiments, the composition is in a dosage form that comprises a functional coating which constitutes about 5% or less of the total weight of the dosage form. In some embodiments, the composition is in a dosage form that comprises a functional coating and the functional coating constitutes from 1 to 5% of the total weight of the dosage form. In some embodiments, the functional coating is comprised of one or more separate coatings or layers. In some embodiments, the one or more separate coatings or layers may be an enteric coating, a time-release coating, a pH-dependent coating or other as well as combinations of these. In some embodiments, the dosage form characteristics comprise one of hardness, thickness, friability, speed of disintegration, speed of dissolution, shape, size, density, coating and combinations thereof. In some embodiments, the dosage form characteristics are modulated by controllably manipulating during production or manufacturing of said composition one of physical mixing specifications, drying time, pressing conditions, environmental parameters and combinations thereof. In some embodiments, the dosage form characteristics comprise a targeted dissolution profile at pH 6.0. In some embodiments, the dosage is divided into two, three, four, or more dosage units. In some embodiments, the selected subject group is a group of selected human subjects. In some embodiments, the composition when administered to a select subject group provides in said selected subject group an improved pharmacokinetic profile through: a reduced variation of $T_{max}$ and equivalent AUC to bi-daily dosing and/or reduced side effects through once a day dosing. In some embodiments, the composition when administered to a selected subject group provides in said selected subject group an average $C_{max}$ within the range of about 100 ng/mL to about 500 ng/mL per 100 mg of SAMe ion, or within a range of 110 ng/mL to about 500 ng/mL per 100 mg of SAMe ion; or within a range of 120 ng/mL to about 500 ng/mL per 100 mg of SAMe ion. In some embodiments, the composition when administered to a selected subject group provides in said selected subject group an average AUC within the range of about 450 ng·h/mL to about 800 ng·h/mL for a 100 mg dosage of SAMe ion. In some embodiments, the composition when administered to a subject provides in the subject one of an average $T_{max}$ or $C_{max}$ with reduced variation or a reduced effective dose in comparison to a SAMe reference data set. In some embodiments, the composition comprises an oral delivery system, or a transmucosal delivery system. In some embodiments, the composition comprises one of tablets, pastes, capsules, granules, caplets, lozenges, pastes, and suppositories. In some embodiments, the composition comprises an oral delivery system. In some embodiments, dissolution of the oral delivery system or dosage form provides about 20-90% release of SAMe after 60 minutes of being in an aqueous buffer having an initial pH of about 6. In some embodiments, dissolution of the oral delivery system or dosage form provides about 25-80% release of SAMe after 60 minutes of being in an aqueous buffer having an initial pH of about 6. In some embodiments, dissolution of the oral delivery system or dosage in a USP II dissolution apparatus in aqueous buffer having initial pH of about 6.0 provides about 30-70% release of SAMe after 60 minutes of being in the buffer phase. According to USP standards for dissolution profiling of an enteric-coated dosage form, a two hour incubation in an acidic/fluid phase precedes incubation in the aqueous buffer. Thus in some embodiments dissolution of the oral delivery system or dosage form provides about 20-90% release of SAMe after 60 minutes of being in an aqueous buffer having an initial pH of about 6, wherein prior to incubation in said aqueous buffer the oral delivery system or dosage form is incubated for two hours in an acidic solution. In some embodiments dissolution of the oral delivery system or dosage form provides about 25-80% release of SAMe after 60 minutes of being in an aqueous buffer having an initial pH of about 6, wherein prior to incubation in said aqueous buffer the oral delivery system or dosage form is incubated for two hours in an acidic solution. In some embodiments, dissolution of the oral delivery system or dosage in a USP II dissolution apparatus in aqueous buffer having initial pH of about 6.0 provides about 30-70% release of SAMe after 60 minutes of being in the buffer phase, wherein prior to incubation in said buffer phase the oral delivery system or dosage form is incubated for two hours in an acidic solution. In some embodiments, the composition comprises a dietary supplement. In some embodiments, the composition comprises a medical food. In some embodiments, there is provided a method of treating a disease condition or disorder, comprising administering to a subject in need of such treatment an effective amount of the composition of described herein. In some embodiments, the subject is human.

There is also provided herein an oral dosage composition comprising a physiologically effective dosage of SAMe in combination with at least one excipient, wherein administration of said composition to a selected subject group produces in said selected subject group an effect comprising one of: a. an average maximum SAMe blood plasma concentration (average $C_{max}$) of at least about 1800 ng/mL for a 1600 mg dosage of SAMe ion; or, b. an average SAMe plasma area under the curve (average AUC) of at least about 7500 ng·h/mL for a 1600 mg dosage of SAMe ion; or, c. an average maximum SAMe blood plasma concentration (average $C_{max}$) of at least about 850 ng/mL and an average SAMe plasma area under the curve (average AUC) of at least about 4000 ng·h/mL for a 800 mg dosage of SAMe ion; or, d. an average maximum SAMe blood plasma concentration (average $C_{max}$) of at least about 400 ng/mL and/or an average SAMe plasma area under curve (average AUC) of at least about 1800 ng·h/mL for a 400 mg dosage of SAMe ion; or, e. an average maximum SAMe blood plasma concentration (average $C_{max}$) of at least about 200 ng/mL and/or an average SAMe plasma area under curve (average AUC) of at least about 900 ng·h/mL for a 200 mg dosage of SAMe ion; or, f. an average maximum SAMe blood plasma concentration (average $C_{max}$) of at least about 100 ng/mL and/or an average SAMe plasma area under curve (average AUC) of at least about 450 ng·h/mL for a 100 mg dosage of SAMe ion. In some embodiments, the at least one excipient is one of matrix materials; binders; lubricants, glidants, coatings, disintegrants, super-disintegrants, polysaccharides, oligosaccharides, polypeptides, proteins, synthetic oligomers, synthetic polymers, monomeric organic molecules, hydrophobic organic molecules, hydrophilic organic molecules, amphoteric organic molecules, inorganic salts, inorganic metals, and combinations thereof. In some embodiments, the composition comprises physical or chemical dosage form characteristics which modulate one of said average SAMe $C_{max}$ and said average SAMe AUC. In some embodiments, the composition is in a dosage form manufactured at a relative humidity of less than 10%. In some embodiments, the composition is in a dosage form that comprises a functional coating and the functional coating constitutes 5% or less of the total weight of the dosage form. In some embodiments, the composition is in a dosage form that comprises a functional coating and the functional coating constitutes from 1 to 5% of the total weight of the dosage form. In some embodiments, the functional coating is comprised of one or more separate coatings or layers. In some embodiments, the one or more separate coatings or layers are each an enteric coating, a time-release coating, a pH-dependent coating or other as well as combinations of these. In some embodiments, the dosage form characteristics comprises one of hardness, thickness, friability, speed of disintegration, speed of dissolution, shape, size, density, coating and combinations thereof. In some embodiments, the dosage form characteristics are modulated by controllably manipulating during production of said composition one of physical mixing specifications, drying time, pressing conditions, environmental parameters, and combinations thereof. In some embodiments, the composition is manufactured under specific conditions comprising one of mixing method (including sieve size, rpm, and milling), drying time, press conditions, environmental parameters and combinations thereof. In some embodiments, the dosage is divided into two, three, four, or more dosage units. In some embodiments, the selected subject group is a selected group of humans. In some embodiments, the composition when administered to a selected subject group provides in said selected subject group an average $C_{max}$ within the range of about 100 ng/mL to about 500 ng/mL per 100 mg of SAMe ion. In some embodiments, the composition when administered to a selected subject group provides in said selected subject group an average AUC within the range of about 450 ng·h/mL to about 800 ng·h/mL for a 100 mg dosage of SAMe ion. In some embodiments, the composition when administered to a subject provides in the subject one of an average $T_{max}$ or $C_{max}$ with reduced variation or a reduced effective dose in comparison to a SAMe reference data set. In some embodiments, there is further provided a method of treating a disease condition or disorder comprising administering to a subject in need of such treatment an effective amount of the composition described herein. In some embodiments, the subject is a human.

Also provided herein is a dietary supplement preparation comprising a physiologically effective dosage of SAMe in combination with at least one excipient, wherein administration of said composition to a selected subject group produces in said selected subject group an effect comprising one of: a. an average maximum SAMe blood plasma concentration (average $C_{max}$) of at least about 1800 ng/mL for a 1600 mg dosage of SAMe ion; or, b. an average SAMe plasma area under the curve (average AUC) of at least about 7500 ng·h/mL for a 1600 mg dosage of SAMe ion; or, c. an average maximum SAMe blood plasma concentration (average $C_{max}$) of at least about 850 ng/mL and an average SAMe plasma area under the curve (average AUC) of at least about 4000 ng·h/mL for a 800 mg dosage of SAMe ion; or, d. an average maximum SAMe blood plasma concentration (average Cmax) of at least about 400 ng/mL and/or an average SAMe plasma area under curve (average AUC) of at least about 1800 ng·h/mL for a 400 mg dosage of SAMe ion; or, e. an average maximum SAMe blood plasma concentration (average Cmax) of at least about 200 ng/mL and/or an average SAMe plasma area under curve (average AUC) of at least about 900 ng·h/mL for a 200 mg dosage of SAMe ion; or, f. an average maximum SAMe blood plasma concentration (average Cmax) of at least about 100 ng/mL and/or an average SAMe plasma area under curve (average AUC) of at least about 450 ng·h/mL for a 100 mg dosage of SAMe ion. In some embodiments, the at least one excipient is one of matrix materials; binders; lubricants; glidants; coatings; disintegrants, super-disintegrants; polysaccharides, oligosaccharides; polypeptides, proteins synthetic oligomers, synthetic polymers, monomeric organic molecules, hydrophobic organic molecules, hydrophilic organic molecules, amphoteric organic molecules, inorganic salts inorganic metals, and combinations thereof. In some embodiments, the composition comprises physical or chemical dosage form characteristics which modulate one of said average SAMe $C_{max}$ and said average SAMe AUC. In some embodiments, the composition is in a dosage form manufactured at a relative humidity of less than 10%. In some embodiments, the composition is in a dosage form that comprises a functional coating and the functional coating constitutes 5% or less of the total weight of the dosage form. In some embodiments, the composition is in a dosage form that comprises a functional coating and the functional coating constitutes from 1 to 5% of the total weight of the dosage form. In some embodiments, the functional coating is comprised of one or more separate coatings or layers. In some embodiments, the one or more separate coatings or layers are each an enteric coating, a time-release coating, a pH-dependent coating or other as well as combinations of these. In some embodiments, the dosage form characteristics comprises one of hardness, thickness, friability, speed of disintegration, speed of dissolution, shape, size, density, coating and combinations thereof. In some embodiments, the dosage form characteristics are modulated by controllably manipulating during production of said composition one of physical mixing specifications, drying time, pressing conditions, environmental parameters and combinations thereof. In some embodiments, the composition is manufactured under specific conditions comprising one of mixing method (including sieve size, rpm, and milling), drying time, press conditions, environmental parameters and combinations thereof. In some embodiments, the selected subject group is a selected group of humans. In some embodiments, the composition when administered to a selected subject group provides in said selected subject group an average $C_{max}$ within the range of about 100 ng/mL to about 500 ng/mL per 100 mg of SAMe ion. In some embodiments, the composition when administered to a selected subject group provides in said selected subject group an average AUC within the range of about 450 ng·h/mL to about 800 ng·h/mL for a 100 mg dosage of SAMe ion. In some embodiments, the composition when administered to a subject provides in the subject one of an average $T_{max}$ or $C_{max}$ with reduced variation or a reduced effective dose in comparison to a SAMe reference data set. In some embodiments, there is provided a method of treating a disease condition or disorder comprising administering to a subject in need of such treatment an effective amount of a composition described herein. In some embodiments, the subject is a human.

Also provided herein is a method for improving the pharmacokinetic parameters of exogenous SAMe administered to a subject, said method comprising administering to the subject a non-parental composition comprising at least one physiologically effective dosage of SAMe in combination with at least one excipient selected to improve the pharmacokinetic parameters of said SAMe in a subject, said pharmacokinetic parameters measurable in the subject by one of a Cmax, an AUC, and combinations thereof in comparison to a selected SAMe reference data set. In some embodiments, the at least one excipient is one of matrix materials; binders; lubricants; glidants; coatings; disintegrants, super-disintegrants; polysaccharides, oligosaccharides; polypeptides, proteins synthetic oligomers, synthetic polymers, monomeric organic molecules, hydrophobic organic molecules, hydrophilic organic molecules, amphoteric organic molecules, inorganic salts inorganic metals, and combinations thereof. In some embodiments, the improvement of the pharmacokinetic parameters of said SAMe is a function of a physical or chemical dosage form characteristic of the composition. In some embodiments, the composition is manufactured at a relative humidity of less than 10%. In some embodiments, the composition is in a dosage form, which includes a functional coating, and the functional coating accounts for 5% or less of the total weight of the dosage form. In some embodiments, the functional coating accounts for 1% to 5% of the total weight of the dosage form. In some embodiments, the physical or chemical dosage form characteristic comprises one of hardness, thickness, friability, speed of disintegration, speed of dissolution, shape, size, coating, density, and combinations thereof. In some embodiments, the composition when administered to a selected subject group provides in the selected subject group an average $C_{max}$ of at least about 1800 ng/mL for a 1600 mg dosage of SAMe ion. In some embodiments, the composition when administered to a selected subject group provides in the selected subject group an average $C_{max}$ of at least about 850 ng/mL and an average SAMe plasma area under the curve (average AUC) of at least about 4000 ng·h/mL for a 800 mg dosage of SAMe ion. In some embodiments, the composition when administered to a selected subject group provides in the selected subject group an average $C_{max}$ of at least about 100 ng/mL per 100 mg of SAMe ion in said physiologically effective dosage. In some embodiments, the composition when administered to a selected subject group provides in the selected subject group an average $C_{max}$ within the range of about 110 ng/mL to about 500 ng/mL per 100 mg of SAMe ion in said physiologically effective dosage. In some embodiments, the composition when administered to a selected subject group provides in the selected subject group one of an average $T_{max}$ with reduced variation or a reduced effective dose in comparison to a SAMe reference data set. In some embodiments, the composition when administered to a selected subject group provides in the selected subject group an average AUC of at least about 7500 ng·h/mL for a 1600 mg dosage of SAMe ion. In some embodiments, the composition when administered to a selected subject group provides in the selected subject group an average AUC of at least about 4000 ng·h/mL for a 800 mg dosage of SAMe ion. In some embodiments, the composition when administered to a selected subject group provides in the selected subject group an average AUC within the range of about 500 ng·h/mL to about 800 ng·h/mL for a 100 mg dosage of SAMe ion. In some embodiments, the subjects comprising the selected subject group are one of humans, livestock animals, exotic animals, avian species, laboratory animals, canines, felines, and primates.

In some embodiments, there is provided a method of treating in a patient a disease or disorder selected from the group consisting of mental and psychiatric disorders, nervous system diseases and disorders, neurological diseases and disorders, conditions associated with injuries to the central nervous system, liver diseases and disorders, cancers, joint diseases and disorders, inflammatory diseases and disorders, autoimmune diseases and disorders, degenerative diseases and disorders, soft-tissue diseases and disorders, pain diseases and disorders, cardiovascular disorders related to hyper-homocysteinemia and hypo-homocysteinemia, genetic disorders related to hyper-methylation and hypo-methylation, gastrointestinal diseases and disorders, and disorders induced in whole or in part by oxidative or free-radical damage, comprising administering to the patient in need thereof a composition as described herein.

There is also provided herein a formulation comprising SAMe, wherein the formulation comprises a mixture of SAMe and at least one excipient and the mixture is produced by combining said SAMe and said excipient at a relative humidity less than about 10%.

There is also provided herein a formulation comprising SAMe, wherein the formulation comprises a mixture of SAMe and at least one excipient, wherein the mixture exhibits a dissolution profile at pH 6.0 suitable to target delivery to the proximal intestine.

There is also provided herein a process of improving the pharmacokinetic profile of a SAMe formulation, comprising manufacturing said SAMe formulation at a relative humidity of less than about 10%.

There is also provided herein a composition for oral administration, comprising SAMe and at least one excipient wherein the formulation exhibits an in vitro dissolution profile in pH 6.0 aqueous solution such that greater than 20% and less than 90% of total SAMe in the composition is dissolved from 30 to 90 minutes of incubation in said pH 6.0 aqueous solution. In some embodiments, the formulation exhibits an in vitro dissolution profile in pH 6.0 aqueous solution such that greater than 25% and less than 80% of total SAMe in the composition is dissolved from 45 to 75 minutes of incubation in said pH 6.0 aqueous solution. Prior to incubation in said pH 6.0 aqueous solution the formulation is incubated for about 2 hours in an acidic phase as according to USP standards for dissolution testing of enteric-coated dosage forms. In some embodiments, the composition is in a dosage form manufactured at a relative humidity of less than 10%. In some embodiments, the composition is in a dosage form that comprises a functional coating and the functional coating constitutes 5% or less of the total weight of the dosage form. In some embodiments, the composition is in a dosage form that comprises a functional coating and the functional coating constitutes from 1 to 5% of the total weight of the dosage form. In some embodiments, the functional coating is comprised of one or more separate coatings or layers that together constitute about 5% or less of the total weight of the dosage form.

There is also provided herein a method for improving the uptake of SAMe, comprising administering to a patient SAMe in a formulation that exhibits an in vitro dissolution profile at pH 6.0, wherein greater than 20% and less than 90% of total SAMe is dissolved between 30 to 90 minutes of incubation in the pH 6.0 aqueous buffer. In some embodiments, the formulation exhibits an in vitro dissolution profile in pH 6.0 aqueous solution such that greater than 25% and less than 80% of total SAMe in the composition is dissolved from 45 to 75 minutes of incubation in the pH 6.0 aqueous buffer. In some embodiments, the composition is in a dosage form manufactured at a relative humidity of less than 10%. In some embodiments, the composition is in a dosage form that comprises an enteric coating and the enteric coating constitutes 5% or less of the total weight of the dosage form. In some embodiments, the composition is in a dosage form that comprises an enteric coating and the enteric coating constitutes from 1 to 5% of the total weight of the dosage form.

For greater clarity all references to dose within this patent refer to dose as the dose of SAMe ion. Pharmacokinetic parameters such as average maximum plasma concentration of SAMe ($C_{max}$) are determined using a bioanalytical method with adequate sensitivity, specificity, ruggedness, stability and repeatability (for example, a qualified liquid chromatography triple quad mass spectrometry based method coupled with a suitable extraction method for the separation of analyte from plasma). AUC values were calculated from 0-24 hours using the trapezoid method and are uncorrected for baseline, endogenous SAMe levels. A suitable "selected subject group" has six or more subjects who are dosed fasted. All members of the "selected subject group" have pharmacokinetic parameters for SAMe that fall within statistically normal ranges (i.e. no outliers) and no member will be included on the basis of non-standard or unusual SAMe absorption or metabolism. The average $C_{max}$ values are derived by averaging the concentration at each time point for all members of the subject group. Use of methods of the invention in vivo provides high $C_{max}$ and/or AUC values in comparison to conventional dosage forms of SAMe.

Some embodiments of the invention also relate to compositions and methods which yield a lower effective dose and/or less variable pharmacokinetic parameters (such as $T_{max}$ values with reduced variation) in comparison to conventional non-parenteral SAMe formulations. A "lower effective dose" or "reduced effective dose" is meant to define a physiologically acceptable dose of exogenous SAMe which results in pharmacokinetic parameters which are equivalent to a significantly higher dose of another non-parenteral SAMe formulation, such as that obtained through administration of a higher dose of one or more currently commercially available SAMe formulations. Formulations such as these which exhibit similar $C_{max}$ and AUC values at lower SAMe doses would have many benefits including a lower pill burden and potentially increased tolerability.

Additional embodiments of the invention also relate to compositions and methods which yield an improved side effect profile in comparison to conventional non-parenteral SAMe formulations. An "improved side effect" or "reduced side effect" or "beneficial side effect" profile is meant to define improved tolerability to administration of exogenous SAMe, such as less frequency and/or reduced intensity of side effects associated with SAMe supplementation.

Some exemplary embodiments of the present invention also relate to a dosing regimen of SAMe of once daily, or QD dosing, which results in improved pharmacokinetic profiles while delivering similar or greater AUC levels of SAMe to the subject in comparison to conventional twice daily or more frequent dosing. In certain embodiments, the effect of once a day dosing is believed to result in the most consistent pharmacokinetic parameter measurements, specifically those of the $C_{max}$ and $T_{max}$. The less variable pharmacokinetic profiles that result from once a day dosing of these formulations allow for more certainty of dosing and exposure by the medical practitioner as well as improved side effect profiles for subjects.

In some embodiments of the present invention formulations which exhibit superior pharmacokinetic profiles in comparison to conventional non-parenteral SAMe dosage forms provide an improved rate of onset of SAMe which may result in enhanced therapeutic outcomes.

Other exemplary embodiments of the invention relate to methods for treating a disease or disorder in a subject and/or improving the nutritional status in a subject, said methods comprising administering to said subject compositions of the invention comprising physiologically effective dosages of SAMe thereby improving the pharmacokinetic profile of SAMe. Improved pharmacokinetic profiles are identified by, for example, an increase in $C_{max}$ and/or AUC values; or alternatively a decrease in effective dose; or pharmacokinetic parameters with reduced variation. Achieving one or more of these criteria would constitute an improvement in the pharmacokinetic profile of SAMe.

DETAILED DESCRIPTION OF THE INVENTION

Figure 1:
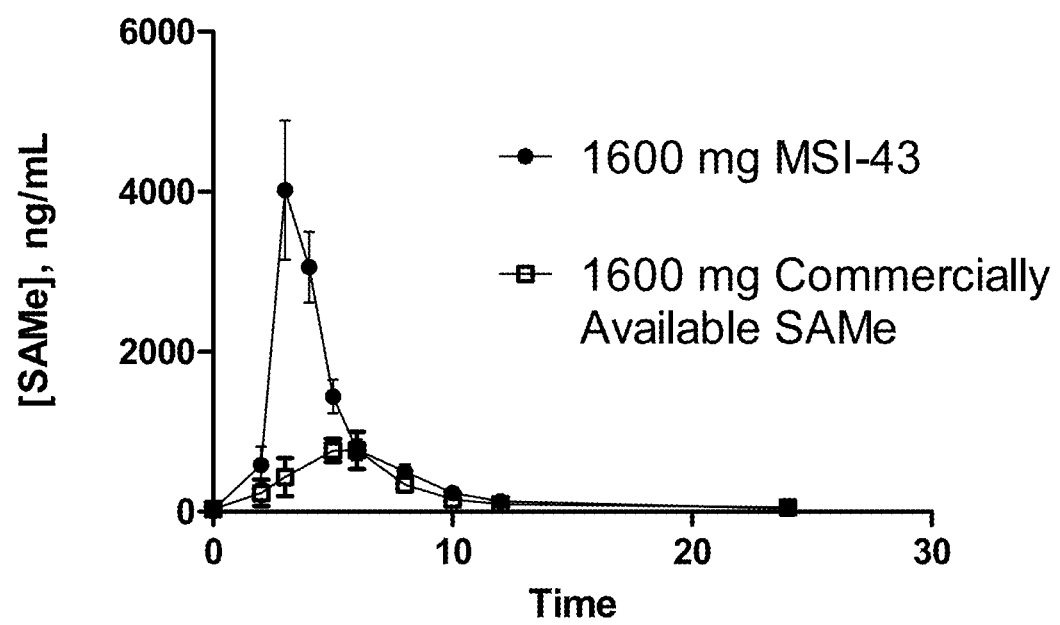
FIG. 1 is a graph of the average SAMe plasma concentration with the standard error of the mean and showing the average maximum plasma concentration ($C_{max}$) of subjects administered a single 1600 mg SAMe ion dose from either a commercially available oral formulation of S-adenosyl methionine tosylate disulphate (open squares) or a single 1600 mg oral dose of MSI-43 of the present invention (closed circles)

The present inventors have discovered that the pharmacokinetic (PK) profile of exogenous SAMe in plasma can be significantly improved by designing dosage forms to release substantial amounts of drug within a particular "window" along the path of dissolution. Surprisingly, formulations which release the vast majority of SAMe extremely early (i.e. those exhibiting an initial "burst" of drug) and those which are slower in their drug release are unable to achieve improved in vivo PK profiles of SAMe. The investigators here identify compositions and methods which are designed to release SAMe within this unexpected "window" of preferred drug release levels. Thus, in some exemplified embodiments, compositions which exhibit improved SAMe PK profiles have targeted amounts of drug release within a particular dissolution "window". This targeted dissolution is such that extensive drug release occurs rapidly over a defined period of time as observed using low pH dissolution studies in vitro. Some exemplary embodiments of the invention therefore also relate to an in vitro screening method of identifying formulations which exhibit improved PK profiles in vivo. Screening is carried out by performing dissolution studies at pH values lower than the standard of pH 6.8.

In other embodiments, compositions which exhibit improved SAMe PK profiles are generated under conditions of very low relative humidity. Additional embodiments of the invention relate to non-parenteral compositions and methods that improve the PK profile of exogenous SAMe and methods of using the same, e.g. for the treatment of various diseases or disorders in a subject and/or improving the nutritional status of a subject. In certain embodiments compositions of the invention are administered to the subject once per day. In some embodiments, administration of compositions of the invention to a subject results in an improved side effect profile of said subject. In other embodiments, compositions of the invention provide rapid onset of exogenous SAMe in comparison to conventional non-parenteral SAMe dosage forms.

Further embodiments of the invention relate to combinations of SAMe with one or more active ingredients that are commonly prescribed or used for treatment of and/or prophylaxis of various diseases or disorders in a subject. Some other embodiments of the invention relate to non-parenteral compositions and methods that improve the PK profile of exogenous SAMe either alone or in combination with one or more additional agents and additionally improve the side effect profile associated with SAMe and/or said one or more additional agents.

"Improved pharmacokinetic profile" or "enhanced pharmacokinetic profile" as used herein refers to one or more of the following criteria in comparison to conventional oral SAMe treatments: 1) high average $C_{max}$ (greater than about 1800 ng/mL when tested at a dose of 1600 mg (SAMe ion)); and/or 2) increased AUC (greater than about 7500 ng·h/mL when tested at a dose of 1600 mg (SAMe ion) or greater than about 4000 ng·h/mL when tested at a dose of 800 mg); and/or 3) pharmacokinetic parameters with reduced variation; and/or 4) reduced effective dose (for example, a $C_{max}$ of at least about 100 ng/mL per 100 mg dose of SAMe ion and/or an AUC of about 450 ng·h/mL per 100 mg dose of SAMe ion). In some embodiments, the invention provides a blood plasma SAMe $C_{max}$ of greater than about 2000 ng/mL, greater than about 3000 ng/mL, or greater than about 3500 ng/mL when tested at a dose of 1600 mg (SAMe ion). In some embodiments, the invention provides a $C_{max}$ of at least about 110 ng/mL per 100 mg dose of SAMe ion, at least about 130 ng/mL per 100 mg dose of SAMe ion, at least about 150 ng/mL per 100 mg dose of SAMe ion, at least about 180 ng/mL per 100 mg dose of SAMe ion, at least about 210 ng/mL per 100 mg dose of SAMe ion, or at least about 240 ng/mL per 100 mg of SAMe ion. In some embodiments, the invention provides an AUC of greater than about 8000 ng·h/mL, greater than about 10000 ng·h/mL, greater than about 11000 ng·h/mL, or greater than about 12000 ng·h/mL when tested at a dose of 1600 mg (SAMe ion). In some embodiments, the invention provides an AUC of at least 500 ng·h/mL per 100 mg SAMe dosed, at least 600 ng·h/mL per 100 mg SAMe dosed, at least 700 ng·h/mL per 100 mg SAMe dosed, or at least 800 ng·h/mL per 100 mg SAMe dosed.

As used herein the term "SAMe" refers to S-adenosyl-L-methionine (or, more simply, "S-adenosylmethionine"). When referring to dose, the amount (typically in mg) refers to the dose of SAMe ion administered. As shown in the structural formula presented earlier, SAMe appears as a charged species, and its ionization state varies with pH. In its solid form, SAMe is most commonly available as a stable salt form, e.g. with p-toluenesulfonic acid alone or in combination with one or more additional salt-forming substances for example, mineral or organic acids and/or amino acids. (See U.S. Pat. No. 3,893,999, incorporated herein by reference in its entirety). Other stable SAMe salts are described in, for example, U.S. Pat. No. 5,128,249, which describes particular stable salts of SAMe. Various morphologies of SAMe are suitable for use in the present invention. Thus, as used herein "SAMe" refers to the stable salts, amorphous forms, semicrystalline forms and crystalline forms of SAMe as well as to the ionic form of SAMe when present in vivo. A "physiologically effective dosage" of SAMe as used herein is meant to include an amount of SAMe which is administered under a defined dosing regimen for either clinical, pharmaceutical, medicinal, veterinary, dietary or nutritional purposes. Thus a "physiologically effective dosage" or a "physiologically acceptable dosage" of SAMe includes a therapeutically effective dosage, a pharmaceutically acceptable dosage, a veterinary acceptable dosage, a nutraceutically acceptable dosage, a dietary acceptable dosage and a nutritionally acceptable dosage of SAMe as well as an acceptable dosage for use as a medical food and all of which are included for use in the present invention. When referring to "medicinal" preparations, purposes or treatments they are meant to include "medical foods". Medical foods are defined by the U.S. Food and Drug Administration as a food which is formulated to be consumed or administered enterally under the supervision of a physician and which is intended for the specific dietary management of a disease or condition for which distinctive nutritional requirements, based on recognized scientific principles, are established by medical evaluation.

Some exemplary embodiments of the present invention relate to non-parenteral compositions and methods of their use for enhancing the effectiveness of a physiologically effective dosage of SAMe utilized as a medical food or dietary or nutritional supplement in a subject.

Some exemplary embodiments of the invention relate to a method for treating and/or prophylaxis in a subject a disease or disorder selected from the group consisting of, but not limited to, a mental or psychiatric disorder (e.g. psychotic/mood or non-psychotic mental disorders exemplified by depression and substance related disorders, respectively), a nervous system disease/disorder (e.g. a central nervous system disease exemplified by Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, and a disorder induced in whole or in part by oxidative or free-radical damage, comprising administering to said subject an exemplary composition of the present invention which provides a physiologically effective amount of exogenous SAMe with an improved PK profile.

Some exemplary embodiments of the present invention relate to non-parenteral compositions and methods which improve the side effect profile associated with a physiologically effective amount of exogenous SAMe.

Other exemplary embodiments of the present invention relate to combinations of SAMe with one or more active ingredients that are commonly prescribed or used for treating and/or prophylaxis in a subject a disease or disorder selected from the group consisting of, but not limited to, those detailed above. In some embodiments administration of improved PK SAMe formulations of the invention with one or more active ingredients that are commonly prescribed or used for treating and/or prophylaxis in a subject a disease or disorder selected from the group described above leads to an improved side effect profile of the subject. In certain embodiments, the side effect profile resulting from use of said one or more active ingredients that are commonly prescribed or used for treating and/or prophylaxis in a subject a disease or disorder selected from the group described above, is improved.

SAMe Formulations for Non-Parenteral Administration

Formulations for non-parenteral administration of drugs/therapeutic agents are typically provided as solid or semi-solid products or dosage forms, exemplified by tablets, capsules or pellets, and generally consist of a core "matrix material" which 'encapsulates' the drug as well as one or more protective coatings. "Product" or "dosage form" as used herein refers to any solid or semi-solid formulation or preparation used for non-parental administration. Non-parenteral formulations or preparations as described herein include oral delivery systems exemplified by tablets, pastes, capsules, granules, caplets, lozenges and the like; and transmucosal or inhaled delivery systems, exemplified by aerosols, irrigants, topical creams, pastes, lozenges, patches, and the like, all of which are well-known and well-documented in the art. These formulations may be administered using a clinical, pharmaceutical or veterinary dosing regimen. Non-parenteral dosage forms may also be provided as medical foods or dietary or nutritional supplements. Non-parenterally administered SAMe formulations may be configured to enable extended release of the formulated SAMe. Co-owned U.S. patent application 2009/0088404, which is incorporated herein by reference, provides novel formulations of extended-release SAMe formulations.

Upon administration, the rate of release of an active moiety from a non-parenteral product can be greatly influenced by the excipients and/or product characteristics which make up the product itself. For example, an enteric coat on a tablet is designed to separate that tablet's contents from the stomach contents to prevent, for example, degradation of the stomach which may induce gastrointestinal discomfort or injury. SAMe and other tablets described in the art are commonly enteric coated. Once the dosage form has transited from the stomach to the duodenum and subsequently the rest of the small intestine the enteric coat is removed due the pH change and the table disintegrates/dissolves according to its intrinsic properties and the dosage form technologies that have been applied. According to the currently accepted conventional understanding, systemic exposure of the active moiety will be relatively insensitive to the small formulation changes. For example, following the conventional understanding, one would expect similar or near similar PK behavior for formulations with an application of enteric coat within the normal range of recommended application thicknesses. Similarly, following the conventional understanding, one would expect comparable behavior for dosage forms prepared within a range of humidity that allowed for the efficient and effective handling of the active moiety through the course of the formulation process. For SAMe as the active moiety, the impact of these processing parameters is expected to be particularly blunted in light of the teaching within the art that SAMe is subject to low bioavailability due to extensive first pass metabolism. Thus one would predict consistent systemic exposure as measured by pharmacokinetics for different enteric coated dosage forms within the normal range of operating parameters as long as active moiety was delivered intact to the site of absorption in the small intestine. However, the investigators here have found that, contrary to conventional understanding, combinations of exogenous SAMe with one or more excipients and/or processing parameters which result in specific product characteristics dramatically affect the pharmacokinetic profile of SAMe and lead to high $C_{max}$ and AUC values in vivo.

Suitable excipients which result in improved pharmacokinetic profiles of SAMe are preferably included in non-parenteral formulations of the invention. More specifically, formulations which include SAMe and one or more suitable excipients, exemplified by matrix materials, binders, lubricants, glidants or disintegrants which aid in modulating the PK profile of administered exogenous SAMe are preferred. Other embodiments of the invention relate to compositions comprising SAMe in combination with one or more suitable excipients and one or more specific product characteristics (such as dissolution or water content) which result in improved pharmacokinetic profiles of SAMe in vivo. Thus, the in vivo performance of non-parenteral SAMe dosage forms/products included herein is based upon the composition of the excipients added during manufacturing and/or the final product characteristics generated through specific processing parameters and methods.

Product or Dosage Form Characteristics

The product or dosage form characteristics which result from the processing methods and/or parameters for generating non-parenteral formulations such as tablets, include, but are not limited to, hardness, thickness, water content, friability, disintegration, dissolution profile(s), shape, size, weight, uniformity and composition. These product characteristics can be modulated in a number of ways and affect the final in vitro and/or in vivo performance of the formulations. As an example, tablets generated by compression or molding processes may have varying degrees of thickness or hardness depending on the processing parameters under which they were made. Product or dosage form characteristics may be a consequence of excipient selection, excipient composition, manufacturing methods applied or a combination of any of these. The combination of excipients as well as product characteristics (including processing methods or processing parameters) of the final dosage form will ultimately determine the pharmacokinetic profile of the active ingredient in vivo. The non-parenterally administered SAMe formulations of the invention may be processed or manufactured under specific conditions such as, for example, mixing methods (including sieve size, rpm, and milling), drying time, press conditions, environmental parameters (e.g. temperature and humidity) and combinations thereof) which themselves modulate the pharmacokinetic profile of SAMe in vivo (i.e. increase the average $C_{max}$ or AUC). In order to quantitatively compare one tablet to another, it is customary to measure several of these product or dosage form characteristics. This is also necessary when attempting to duplicate multiple batches.

Surprisingly, the present investigators found that a specific "window" of dissolution (i.e. a particular amount of drug release over a certain time frame) correlated with those formulations of the invention which exhibited an improved SAMe PK profile in vivo. Although dissolution studies are commonly utilized to characterize non-parenteral formulations, testing is standard using a buffer phase which is at pH 6.8 to best represent the pH of the distal small intestine. In addition, dissolution profiles are commonly referred to in the art as either "fast" or "slow"; however, the present investigators have identified that in fact a specific "window" of fast dissolution leads to levels of SAMe in the plasma not previously reported in these arts.

Dissolution and drug release from formulations depends on many factors including the solubility and concentration of the active ingredient, the nature and composition of the excipients, content uniformity, water content, product shape and size, porosity, disintegration time and other factors. The release of a drug or active ingredient from a final dosage form in vitro is typically characterized by its dissolution profile under standardized conditions (using United States Pharmacopeia (USP) or similar accepted methods for reference) and at pH 6.8 as mentioned above. The dissolution profile shows the amount of drug released over time into the test media under specified conditions. Standard conditions make use of buffers at pH 6.8 in order to best mimic the pH of distal small intestine. The dissolution test method for enteric dosage forms involves incubation of the formulation in a first acidic phase for two hours and is then transferred to the aqueous buffer phase (pH 6.8). Time points for measuring drug release begin at this two-hour time period (i.e. when first transferred into the aqueous buffer phase). Investigators here found that when dissolution profiles of multiple SAMe formulations of the invention are analyzed under conditions of pH 6.8, all formulations show "fast" dissolution and their dissolution profiles cannot be distinguished from one formulation to the next. However, when the dissolution studies were conducted using a pH 6.0 buffer, which best mimics that the pH of a specific region of the upper small intestine where SAMe is absorbed, there is significant differentiation between the formulations which are "fast" to dissolve and release drugs. Moreover, pharmacokinetic analysis of these formulations in vivo showed that formulations of the invention dissolving rapidly within a specific "window", as seen in the pH 6.0 dissolution profiles, correlated with those formulations exhibiting very high $C_{max}$ and AUC values (see Examples 2-3).

Some embodiments of the invention thus relate to improved pharmacokinetic SAMe compositions which show targeted dissolution in a buffer phase of pH 6.0. Preferably, between 25-80% SAMe is released after one hour of incubation in the buffer phase; more preferably about 30-70% SAMe is released within one hour of incubation in the buffer phase; and even more preferably, about 30-60% SAMe is released within one hour of incubation in the buffer phase.

Excipients and Processing Parameters Suitable for Use in the Invention

Excipients are usually grouped by their function such as: disintegrants, diluents, binders, lubricants, glidants, coatings, coloring agents or flavoring agents, and the same excipient may be used for more than one function in a given oral formulation. Commonly used pharmaceutically acceptable excipients include water, magnesium stearate, starch, lactose, microcrystalline cellulose, stearic acid, sucrose, talc, silicon dioxide, gelatin, acacia and dibasic calcium phosphate (Baldrick, P. (2000) *Regul. Toxicol. Pharmacol.* October 32(2):210.) Excipients are combined with active ingredients for example to enhance appearance, improve stability, aid processing or aid disintegration after administration, but many other excipient functions are known in the art that can be applied to SAMe oral dosage forms. Classes of excipients which are often used and suitable for use in the present invention include but are not limited to, natural, modified-natural or synthetic mono-, oligo- or polysaccharides where oligo- and polysaccharides may or may not be physically or chemically crosslinked; natural, modified-natural or synthetic mono-, oligo- and polypeptides or proteins where oligo- and polypeptides and proteins may or may not be physically or chemically crosslinked; synthetic oligomers and polymers that may or may not be physically or chemically crosslinked; monomeric, hydrophobic, hydrophilic or amphoteric organic molecules; inorganic salts or metals; and combinations thereof. Accordingly, SAMe may be combined with any excipient(s) known in the art that allows tailoring its performance during manufacturing as well as its in vitro and in vivo performance. Many of these excipients may be utilized to tailor the dissolution profiles of SAMe formulations.

Disintegrants

Disintegrants are added to non-parenteral formulations to induce breakup of the product or dosage form (i.e. tablet or capsule) when it comes in contact with aqueous fluid in order to help release the drug. The objectives behind addition of disintegrants are to increase surface area of the product fragments and to overcome cohesive forces that keep these particles together in a formulation. They do this by promoting wetting and swelling of the dosage form so that it breaks up in the gastrointestinal tract. Some binders such as starch and cellulose also act as disintegrants. Other disintegrants are clays, cellulose derivatives, algins, gums and crosslinked polymers. Another group of disintegrants called "super-disintegrants" are often utilized. These materials are effective at low (2-5%) concentrations. "Super-disintegrants" which may be suitable for use in the present invention include, but are not limited to, sodium starch glycolate (SSG), croscarmellose sodium or crosprovidone.

The invention therefore also relates to compositions comprising SAMe and one or more disintegrants or "super-disintegrants" which improve the pharmacokinetic profile of SAMe in vivo.

Binders

The binding material which holds the bulk of the product together and also helps maintain the product in a desired shape is known as a "binder" or "granulator". Binders suitable for use in the present invention are exemplified by, but are not limited to, sugars, gelatin, gums, microcrystalline cellulose and modified celluloses, waxes or synthetic polymers like polyethylene glycol or polyvinyl pyrrolidone.

Some embodiments of the invention may include improved pharmacokinetic compositions comprising SAMe and one or more binders.

Lubricants

Additional excipients often utilized in product formulations are lubricants. These are substances which aid in the manufacturing process as they help minimize clumping of the products and also help release them from the manufacturing machinery. The most common "lubricant" used for oral formulations is magnesium stearate; however, other commonly used product lubricants include talc, calcium stearate, stearic acid (stearin), hydrogenated vegetable oils, sodium benzoate, leucine, carbowax 4000 and sodium stearyl fumarate all of which may be suitable for use in the present invention.

Further exemplary embodiments of the invention also relate to improved pharmacokinetic compositions comprising SAMe and one or more lubricants.

Glidants

Glidants also referred to as "flow-aids", help to keep the powder making up the products flowing as the products are being made, stopping them from forming lumps. Examples of commonly used glidants which may be suitable for use in the invention include colloidal silicon dioxide, talc, calcium silicate and magnesium silicate.

Additional embodiments of the invention relate to improved pharmacokinetic compositions comprising SAMe and one or more glidants.

Coatings

An outer coating is typically applied to oral dosage forms in order to mask taste, odor or color; provide physical or chemical protection for the active ingredient/drug; control the release of the active ingredient from the formulation; protect the active ingredient from the harsh environment of the stomach (i.e. enteric coating); or protect the subject from unwanted gastrointestinal side effects. Prior to applying the external coating, a seal coating may first be applied. Seal coatings act to smooth the product surfaces, enhance the adherence of the final, outer coat and/or to protect the active ingredient from premature degradation. The type and/or thickness of the seal coat or the final coating(s) may be varied in order to alter product characteristics, such as dissolution. Typically, the external or functional coatings are targeted to be about 4-10% by weight and seal coats are targeted to be about 1-5%, preferably about 2%, by weight. Seal coats are generally thought of as "non-functional" in that they are not utilized to control timing or placement of release of the active ingredient; however, it is considered that certain seal coatings may act as such "functional" coatings. For the purpose of the present invention, "functional coatings" are intended to include enteric coatings, time-release coatings, pH-dependent coatings or other which control the timing or placement of release of the active ingredient. In some exemplified embodiments of the invention, the one or more separate coatings or layers of the functional coating together constitute 5% or less of the total dosage form targeted by weight. In preferred embodiments the functional coating is an enteric coating and even more preferably the enteric coating is about 3-4% targeted by weight.

Some embodiments of the invention may include improved pharmacokinetic compositions comprising SAMe and one or more coatings which alter the pharmacokinetic parameters of exogenous SAMe. Other embodiments of the invention may include improved pharmacokinetic compositions comprising SAMe and one or more coatings which alter the in vitro dissolution profile of SAMe. Specific exemplified embodiments of the invention include improved pharmacokinetic compositions comprising SAMe and one or more coatings which result in a dissolution profile exhibiting about 25-80% SAMe released after one hour of incubation in the buffer phase; more preferably about 30-70% SAMe released within one hour of incubation in the buffer phase; and even more preferably, about 30-60% SAMe released within one hour of incubation in the buffer phase.

The suitability of a particular excipient, such as, for example, a "matrix material", "disintegrant", "super-disintegrant" "binder", "lubricant", "glidant", or "coating" may be identified by analyzing the in vivo pharmacokinetics of formulations containing the excipient and SAMe. Alternatively, in vitro analysis of one or more excipients using a series of standard in vitro techniques which are well known in the art may be used to pre-screen excipients and ultimately provide a means to predict in vivo pharmacokinetic profiles. Furthermore, the use of references in the art may also provide insight into potentially suitable pharmaceutically or nutritionally acceptable excipients (such as a "matrix material", "disintegrant", "binder", "lubricant", "glidant", or "coating") for use in the present invention. Preferably, in vitro analysis of one or more excipients using dissolution studies conducted with a buffer pH of less than 6.8 may be used to pre-screen excipients and ultimately provide a means to predict in vivo pharmacokinetic profiles.

Processing Methods and Parameters

Processing methods and/or parameters which may be modified in order to improve the pharmacokinetic profile and/or alter the dissolution profile of SAMe formulations include but are not limited to: relative humidity, temperature, drying time and other environmental parameters.

Some exemplary embodiments of the invention are generated under low humidity conditions, typically less than or equal to about 35%, and preferably less than or equal to about 15-25%, and more preferably less than or equal to about 10%. Other exemplary embodiments of the invention are generated under manufacturing conditions wherein the temperature is maintained between about 15-35° C. Other exemplary embodiments of the invention are manufactured using a drying time of about 4-24 hours. Additional embodiments of the invention make use of SAMe compositions comprising low water content. "Low water content" is preferably those formulations containing less than or equal to about 5% water, more preferably less than or equal to about 3.5% water and even more preferably less than or equal to about 1.5% water. In one way, water content is altered by controlling the relative humidity during the manufacturing process.

Exemplary embodiments of the invention relate to compositions comprising exogenous SAMe and one or more suitable excipients and/or processing parameters which improve the pharmacokinetic profile of SAMe in vivo. In some embodiments, the improved pharmacokinetic profile is identified by an average $C_{max}$ of SAMe of at least about 1800 ng/mL, at least about 1900 ng/mL or at least about 2000 ng/mL, when tested at a 1600 mg dose of SAMe ion; an AUC of at least about 7500 ng·h/mL, 8000 ng·h/mL, 8500 ng·h/mL, or 9000 ng·h/mL when tested at a 1600 mg dose of SAMe ion; a $T_{max}$ or $C_{max}$ with reduced variation; a reduced effective dose, or combinations thereof. In some preferred embodiments, the improved pharmacokinetic profile is an average $C_{max}$ of SAMe of at least 1800 ng/mL for a 1600 mg dose of SAMe ion. In some embodiments, the improved pharmacokinetic profile is identified by an average $C_{max}$ of SAMe of at least about 800 ng/mL, 825 ng/mL, 850 ng/mL, 875 ng/mL, 900 ng/mL, at least about 950 ng/mL or at least about 1000 ng/mL, when tested at a 800 mg dose of SAMe ion; an AUC of at least about 3000 ng·h/mL, 3250 ng·h/mL, 3500 ng·h/mL, or 3750 ng·h/mL when tested at a 800 mg dose of SAMe ion; a $T_{max}$ or $C_{max}$ with reduced variation; a reduced effective dose, or combinations thereof. In some embodiments, the improved pharmacokinetic profile is identified by an average $C_{max}$ of SAMe of at least about 400 ng/mL, 425 ng/mL, 450 ng/mL, at least about 475 ng/mL or at least about 500 ng/mL, when tested at a 400 mg dose of SAMe ion; an AUC of at least about 1500 ng·h/mL, 1550 ng·h/mL, 1600 ng·h/mL, or 1650 ng·h/mL when tested at a 400 mg dose of SAMe ion; a $T_{max}$ or $C_{max}$ with reduced variation; a reduced effective dose, or combinations thereof. In some embodiments, the improved pharmacokinetic profile is identified by an average $C_{max}$ of SAMe of at least about 400 ng/mL, at least about 450 ng/mL or at least about 500 ng/mL, when tested at a 400 mg dose of SAMe ion; an AUC of at least about 1500 ng h/mL, 1550 ng·h/mL, 1600 ng·h/mL, or 1650 ng·h/mL when tested at a 400 mg dose of SAMe ion; a $T_{max}$ or $C_{max}$ with reduced variation; a reduced effective dose, or combinations thereof. The improved pharmacokinetic profile may also be identified by an average $C_{max}$ of SAMe of at least about 100 ng/mL per 100 mg dose of SAMe ion. Similarly, the improved pharmacokinetic profile may also be identified by an AUC of about 450 ng·h/mL per 100 mg dose of SAMe ion.

Dosing with Formulations Exhibiting Improved Pharmacokinetic Profiles of SAMe

In some embodiments the improved pharmacokinetic SAMe formulations of the present invention are expected to be utilized to provide nutritional support, or dietary supplement health improvements including, but not limited to, mood improvement, joint health and liver function. In some exemplary embodiments the disorder is related to the dietary management of a disease through additional supplementation of SAMe which cannot be reached through diet (i.e. a "medical food".)

The improved pharmacokinetic SAMe formulations of the present invention are suitable for therapeutic administration relating to a variety of physiological disorders and disease states, exemplified by, a mental or psychiatric disorder (e.g. psychotic or non-psychotic mental disorders exemplified by depression and substance abuse disorders, respectively), a nervous system disease/disorder (e.g. a central nervous system disease exemplified by Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper- or hypo-methylation, a gastrointestinal disease/disorder, a cardiovascular disease/disorder, and a disorder induced in whole or in part by oxidative or free-radical damage.

Some embodiments of the present invention relate to therapeutic use of the exemplary compositions disclosed herein for treatment of a mental or psychiatric disorder selected from the group consisting of anxiety disorders, depressive disorders, eating disorders, bipolar disorder, abuse disorders, dependence disorders, Axis II disorders, and psychosis. In some exemplary embodiments, the mental or psychiatric disorder is an anxiety disorder selected from the group consisting of generalized anxiety disorder, post-traumatic stress disorder, social anxiety disorder, panic disorder, Schizophrenia and obsessive compulsive disorder. In some exemplary embodiments, the mental or psychiatric disorder is a depressive disorder selected from the group consisting of major depressive disorder, multi-infarct dementia, minor depression, postpartum or late-life depression (and the like), Parkinson's depression, HIV-associated depression, brief recurrent depression, dysthymia or depression NOS (Not Otherwise Specified). In some exemplary embodiments, the mental or psychiatric disorder is an eating disorder selected from the group consisting of bulimia nervosa, anorexia nervosa, binge eating disorder, obesity, or eating disorder NOS. In some exemplary embodiments, the mental or psychiatric disorder is bipolar disorder, an abuse disorder or a dependence disorder, including abuse of, or dependence on, alcohol, nicotine, cocaine, codeine, oxycodone, hydrocodone or other opiates. In some exemplary embodiments, the mental or psychiatric disorder is an Axis II disorder selected from borderline personality disorder.

In some exemplary embodiments, the disorder is a comorbid disorder, such as comorbid depression arising in a subject who is undergoing treatment for one or more diseases or disorders such as but not limited to, cancer, Parkinson's and HIV. In certain embodiments the comorbid disorder is caused by one or more therapies being utilized to treat said one or more diseases or disorders.

In some exemplary embodiments, the disorder is a nervous system disorder, including a central nervous system (CNS) disorder such as Parkinson's disease (and associated Parkinson's depression), Alzheimer's disease, Angelman Syndrome (genetic disorder), Multiple Sclerosis (MS) and pre-dementia and/or cognitive impairment.

In some exemplary embodiments, the disorder is a result of an injury to the CNS such as spinal cord injury or brain damage, memory loss, cognitive impairment and/or learning disability.

In some exemplary embodiments, the disorder is a liver disorder selected from the group consisting of alcoholic liver disease, fatty liver disease (non-alcoholic) hepatitis (both viral and non-viral), liver cancer, oxidative liver disease, HISS-dependent insulin resistance, cholestasis and cirrhosis.

In some exemplary embodiments, the disorder is a cancer selected from the group consisting of cancers occurring in one or more of the liver, colon, rectum, ovaries, urethra, testicles, bladder, breast, stomach, esophagus, pancreas, head and neck, lung, blood, skin (such as actinic keratosis, basal cell cancer, superficial basal cell cancer, squamous cell cancer, and melanoma) and adenocarcinomas.

In some exemplary embodiments, the disorder is a joint disorder such as, for example, arthritis and osteoarthritis.

In some exemplary embodiments, the disorder is an inflammatory disorder selected from the group comprising systemic lupus erythematosis, Reye's syndrome, rheumatic fever, allergic rhinitis, myasthenia gravis, temporal arteritis, vasculitis, psoriasis, atopic dermatitis, rosacea, eczema, alopecia universalis, scleroderma, pemphigus, contact dermatitis, ankylosing spondylitis, dermatomyositis, polymyositis, celiac sprue, Guillain-Barré syndrome, multi-infarct dementia, post-cerebral vascular accident reperfusion damage, Addison's disease, Hashimoto's thyroiditis, asthma, upper respiratory inflammation symptoms, chronic bronchitis, atherosclerosis, pernicious anemia, autoimmune hepatitis, prostatitis, pelvic inflammatory disease, Goodpasture's syndrome, Wegener's granulomatosis, chronic nephritis, Sjogrens syndrome, or allergic conjunctivitis.

In some exemplary embodiments, the disorder is a gastrointestinal disorder such as inflammatory bowel disease (IBD), Crohn's disease or ulcerative colitis (UC).

In some exemplary embodiments, the disorder is a soft tissue disease such as fibromyalgia.

In some exemplary embodiments, the disorder is a pain disorder such as fibromyalgia, chronic headaches, shingles, reflex sympathetic dystrophy and polyneuropathy.

In some exemplary embodiments, the disorder is a cardiovascular disorder which is related to hyper- or hypo-homocysteinemia such as coronary heart disease, stroke, peripheral vascular disease and atherosclerotic disease.

In some exemplary embodiments, the disorder is related to a genetic or medical condition related to a deficiency of the methylation pathway such as methylenetetrahydrofolate reductase deficiency.

In some exemplary embodiments, the etiology of the disorder may include oxidative or free-radical damage, and is selected from the group comprising chronic fatigue syndrome, temporal arteritis, vasculitis, multi-infarct dementia, chronic emphysema, ischemia-reperfusion injury, chronic nephritis or vascular depression.

In some embodiments the improved pharmacokinetic SAMe formulations of the present invention are expected to exhibit an improved side effect profile when utilized to provide nutritional support or dietary supplement health improvements or for therapeutic administration relating to a variety of physiological disorders and diseases such as those listed above. Side effect which may be improved upon include, but are not limited to, gastrointestinal (e.g. nausea, loose stools or constipation); insomnia; restlessness; sexual dysfunction; lower homocysteine levels; cardiovascular side effects (e.g. heart palpitations); nervousness; loss of appetite; dry mouth; dizziness and headaches.

The improved PK SAMe formulations of the invention provide an increase in SAMe plasma levels which are significantly improved in comparison to conventional non-parenteral SAMe dosage forms. There are many potential benefits of this increase in exposure of SAMe to the body including reaching a more therapeutically effective amount of SAMe (such as those resulting from parenteral SAMe administration) which may be necessary to achieve and/or improve a clinical benefit to one or more of the diseases/disorders listed above. Thus, in some embodiments of the invention provided are SAMe formulations which exhibit rapid-onset of treatment for one or more of the diseases/disorders listed above.

In some embodiments the improved pharmacokinetic SAMe formulations of the present invention exhibit average SAMe AUC values of at least about 7500 ng·h/mL per day and/or an average $C_{max}$ of about 1800 ng/mL per day. In other embodiments, average SAMe AUC values of at least about 7500 ng·h/mL per day and/or an average Cmax of about 1800 ng/mL per day lead to improved efficacy in comparison to treatment with conventional exogenous SAMe formulations. These improved $C_{max}$ and/or AUC values may be achieved using a number of dosing regimens and thus may result from a SAMe ion dose which is less than 1600 mg and may be a result of administration of one or multiple SAMe oral dosage forms over the course of 24 hours.

Suitable subjects for dosing according to the methods and compositions of the invention include warm-blooded mammals such as humans, domestic or exotic animals or livestock; domesticated avian subjects such as chickens and ducks; and laboratory animals suitable for research use. When used for treating a disease or disorder in a subject, various symptoms of specific physiological disorders and disease states are contemplated as being treatable within the context of the present invention and details of which are set forth below. However, it is to be recognized that the understanding of various disease states by those of skill in the art is not static and this is the same for performance variables related to nutritional supplementation. Thus, though the description above is intended to be illustrative of the various disorders, disease states, symptoms or performance variables that may be treated using the improved pharmacokinetic SAMe formulations according to the present invention, a person skilled in these arts will be expected to apply such knowledge.

Dosing with Multiple Dosing Units

Some exemplary embodiments of the present invention relate to treatment of and/or prophylaxis of one or more diseases in a subject wherein the treatment of and/or prophylaxis of one or more diseases and/or disorders comprises administering to the subject a physiologically effective dosage comprising S-adenosyl methionine (SAMe), or a proprietary salt thereof, which exhibits an improved pharmacokinetic profile in vivo.

In some exemplary embodiments, the dosing schedule may be divided between multiple daily doses. Multiple daily doses need not be identical and may comprise one or more dosage forms in combination. In some exemplary embodiments, the improved pharmacokinetic SAMe may be divided into two or more daily doses. Each dose may be administered as a single dosage unit exemplified by a single tablet, capsule or caplet, or alternatively may be divided into multiple dosage units. In some embodiments, a twice-daily dose of from about 100 to about 1600 mg of SAMe ion per dose may be divided into one to four dosage units of from about 100 to about 800 mg of SAMe ion per unit. In each case, the form of the dosage unit may be a capsule, a tablet, a caplet or an extended release dosage unit and the like. As mentioned previously, SAMe API is supplied as a molecular entity comprising an ion along with several counter-ions and when referring to SAMe dosing, it is currently accepted in the art that the numerical dose (usually in milligrams) refers to the amount of SAMe ion which is administered. Therefore, a "400 mg SAMe tablet" is referring to a tablet which contains 400 mg of the SAMe ion.

Conventional SAMe dosing generally administers up to 1600 mg of SAMe ion per day (800 mg twice daily). Tablets are most often available commercially in 200 mg and 400 mg (SAMe ion) doses which require subjects to ingest 4-8 tablets per day. This is inconvenient with respect to the amount of time needed as well as the potential error in consistent dosing (i.e. if a dose is missed). The present invention has identified novel compositions and methods which reduce the effective dose of SAMe and/or eliminate the need to dose twice or more daily. By improving the pharmacokinetic profile, a new method of SAMe therapy is available which potentially lowers the amount of SAMe dose required to elicit an effective response by providing compositions comprising one or more suitable excipients or final dosage form characteristics which either increase the average $C_{max}$ or AUC or reduce the variation in pharmacokinetic parameters. These exemplary "low dose" formulations may provide a lower daily pill count which is beneficial to those taking SAMe as it will reduce the time, cost and inconvenience of self-administering large doses. It is expected that lower dosing will also lead to an improved side effect profile when compared to doses of other SAMe products which exhibit similar PK profiles. Thus in some embodiments, provided are SAMe compositions which improve the side effect profile of exogenous SAMe formulations.

In additional exemplary embodiments, the effective dose is administered on a once a day basis. In some embodiments, the once a day dose may be administered in a single dosage unit exemplified by, a single tablet, capsule, or caplet. In other exemplary embodiments, the single dose may be administered as multiple tablets, capsules or caplets taken at one time. In some embodiments, for instance, a dosage of about 400 to 3200 mg of SAMe per day may be divided into two, three, four or more tablets, capsules or caplets of about 100 to 1600 mg of SAMe per unit dose. In some preferred embodiments, the daily dose may comprise two, three or four tablets, capsules or caplets of about 100 to 800 mg of SAMe per dose. Suitable dosage regimens included are: four units of about 200 or 400 mg SAMe per unit; three units of about 100, 150, 200, 300, 400, 600, 800 or 1,000 mg of SAMe per unit; two units of about 200, 400, 800 or 1600 mg per unit.

In certain embodiments of the invention, the effect of once a day dosing is believed to result in the most consistent pharmacokinetic parameter measurements, specifically the $C_{max}$ and $T_{max}$. The "more reliable" pharmacokinetic profile which results from once a day dosing of these formulations allows for improved knowledge of dosing by the medical practitioner as well as improved pharmacokinetic profiles with regard to the time of day when the subjects experience the highest systemic exposure of SAMe ($C_{max}$) which is anticipated to give rise to an improvement in the side effect profiles of these subjects. Traditionally, SAMe dosing is administered twice daily on a fasted stomach for the initial dose. Because subjects are fasting, the first dose is generally given early in the morning (i.e. 8:00 am) prior to food intake. The second dose is then given 8 hours later (i.e. 4:00 pm), typically to a non-fasted stomach. A strong "food affect" is routinely observed which is characterized by a delay in the $T_{max}$ such that the $C_{max}$ is not achieved until normal sleep hours (often 11:00 pm to 2:00 am). Insomnia and other sleep-related events are often reported for many conventional SAMe formulations and this may occur because of the nighttime $C_{max}$ caused by the second dose and the corresponding stimulatory effects of SAMe. In contrast, once a day dosing in the morning using formulations of the invention results in the delivery of equivalent or higher total daily amounts of SAMe (i.e. similar AUC values) yet with the potential for reduced insomnia side effects likely because the $T_{max}$ and $C_{max}$ are achieved during normal waking hours.

Therefore some exemplary embodiments of the present invention relate to compositions comprising SAMe in combination with at least one suitable excipient or product characteristic, wherein said compositions are administered using a once a day dosing regimen. In some embodiments, the SAMe compositions are administered pre-prandially, e.g. before breakfast, thus on a fasted stomach. Certain embodiments also relate to compositions comprising SAMe in combination with at least one suitable excipient or product characteristic, wherein said compositions exhibit a reduced effective dose of the administered physiologically effective dosage of SAMe. Preferably, such compositions achieve an enhanced pharmacokinetic profile such as, for example, an average maximum SAMe blood plasma concentration (average $C_{max}$) of at least about 100 ng/mL per 100 mg of SAMe ion when administered in vivo.

Combinations of SAMe with Other Active Ingredients

Some exemplary embodiments of the present invention relate to combinations of SAMe with one or more active ingredients that are commonly prescribed or used for treating and/or prophylaxis in a subject a disease or disorder selected from the group consisting of, but not limited to, a mental or psychiatric disorder (e.g. psychotic or non-psychotic mental disorders such as depression and substance abuse disorders, respectively), a nervous system disease/disorder (e.g. a central nervous system disease such as Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper or hypo methylation, a gastrointestinal disease/disorder, a cardiovascular disease/disorder, and a disorder induced in whole or in part by oxidative or free-radical damage, comprising administering to said subject an exemplary composition of the present invention which improves the pharmacokinetic profile of a physiologically effective amount of exogenous SAMe.

Additionally, combinations of SAMe with one or more active ingredients as detailed above may act to ameliorate the side effects associated with said one or more active ingredients. Combinations with SAMe may be co-administered or taken separately and need not be taken at the same time.

Other embodiments of the present invention relate to combinations of SAMe with one or more active ingredients that are commonly prescribed or used for treatment of and/or prophylaxis of mental or psychiatric disorders in a subject include, but are not limited to, tricyclic antidepressants (TCAs), tetracyclic antidepressants, aminoketones, phenylpiperazines, selective serotonin reuptake inhibitors (SSRIs), monoamine oxidase inhibitors (MAOIs), serotonin-norepinephrine reuptake inhibitors (SNRIs), norepinephrine-serotonin reuptake inhibitors (NSRIs), dopamine reuptake inhibitors, norepinephrine-dopamine reuptake inhibitors, norepinephrine reuptake inhibitors, selective serotonin reuptake enhancers, noradrenergic and serotonin specific antidepressants, substance P receptor antagonists, neurokinin receptor antagonists such as saredutant, corticotrophin release factor antagonists such as mifepristone, atypical antipsychotics such as aripiprazole, commonly used antidepressant augmenters such as lithium, triple reuptake inhibitors and the like.

Some embodiments of the present invention relate to combinations of SAMe with one or more device therapies that are commonly prescribed or used for treatment of and/or prophylaxis of mental or psychiatric disorders in a subject include, but not limited to ECT (electro convulsive therapy) and electric shock therapy.

Some embodiments of the present invention relate to combinations of SAMe with one or more active ingredients that are commonly prescribed or used for treatment of and/or prophylaxis of a nervous system disease/disorder in a subject include, but are not limited to anticonvulsants such as pregabalin, α-amino-3-hydroxy-5-methyl-4-isoxazolepropionic acid (AMPA) receptor antagonists, methylphosphonate (NMPA) receptor antagonists, histamine receptor antagonists, nitric oxide (NO) modulators, glutamate receptor antagonists, acetylcholinesterase inhibitors, dopamine agonists, N-methyl-d-aspartate (NMDA) receptor antagonists such as memantine, cholinesterase inhibitors such as donepezil, neuroprotectants, nootropic agents, CNS modulators, antiamyloidogenics.

Some embodiments of the present invention relate to combinations of SAMe with one or more active ingredients that are commonly prescribed or used for treatment of and/or prophylaxis of a liver disorder in a subject include, but are not limited to, antiviral medication such as alpha interferon, ribavirin, lamivudine, steroids, antibiotics and zinc acetate.

Some embodiments of the present invention relate to combinations of SAMe with one or more active ingredients that are commonly prescribed or used for treatment of and/or prophylaxis of a cancer in a subject include, but are not limited to, chemotherapeutic agents, drug resistance modulators, monoclonal antibodies, cytokines (e.g. interferons and interleukins), immunocytokines, growth factors, chemoprotectants, vaccines and other biological response modifiers.

Some embodiments of the present invention relate to combinations of SAMe with one or more active ingredients that are commonly prescribed or used for treatment of and/or prophylaxis of a joint or inflammatory disease/disorder in a subject include, but are not limited to, analgesics, non-steroidal anti-inflammatory drug compounds (NSAID), disease-modifying antirheumatic drugs (DMARDs), corticosteroids, anakinra (an interleukin-1 receptor antagonist), COX-2 inhibition, gamma-aminobutyric acid-B (GABAB) receptor agonists, such as baclofen, GABAA potentiating drugs, such as the benzodiazepines tumor necrosis factor (TNF)-inhibiting drugs, and other drugs that modify the immune response (immunosuppressive drugs).

Some embodiments of the present invention relate to combinations of SAMe with one or more active ingredients that are commonly prescribed or used for treatment of and/or prophylaxis of an autoimmune disease/disorder in a subject include, but are not limited to, DMARDs, corticosteroids, anakinra (an interleukin-1 receptor antagonist), TNF-inhibiting drugs, and other drugs that modify the immune response (immunosuppressive drugs).

Some embodiments of the present invention relate to combinations of SAMe with one or more active ingredients that are commonly prescribed or used for treatment of and/or prophylaxis of a degenerative disease/disorder in a subject include, but are not limited to, NSAIDs, COX-2 inhibition, GABAB receptor agonists, such as baclofen, and GABAA potentiating drugs, such as the benzodiazepines.

Some embodiments of the present invention relate to combinations of SAMe with one or more active ingredients that are commonly prescribed or used for treatment of and/or prophylaxis of a soft tissue disease/disorder in a subject include, but are not limited to, milnacipram, pregabalin, SNRIs, NSRIs, muscle relaxers, sedatives, painkillers, and NSAIDs.

Some embodiments of the present invention relate to combinations of SAMe with one or more active ingredients that are commonly prescribed or used for treatment of and/or prophylaxis of a genetic disease/disorder related to hyper or hypo methylation in a subject include, but are not limited to methionine, MTA (5'-deoxy-5'-(methylthio) adenosine), and other SAMe metabolites.

Some embodiments of the present invention relate to combinations of SAMe with one or more active ingredients that are commonly prescribed or used for treatment of and/or prophylaxis of a gastrointestinal disease/disorder in a subject include, but are not limited to, 5-Aminosalicylic acid (5-ASA) medications, Corticosteroids (prednisone), immunomodulatory medications such as Azathioprine (Immuran), 6-Mercaptopurine (6-MP), Methotrexate and Cyclosporine (Sandimmune), commonly used antibiotics such as Metronidazole (Flagyl) and Ciprofloxacin (Cipro) and biologic agents such as Infliximab (Remicade).

Some embodiments of the present invention relate to combinations of SAMe with one or more active ingredients that are commonly prescribed or used for treatment of and/or prophylaxis of a cardiovascular disease/disorder in a subject include, but are not limited to, statins, angiotensin-converting enzyme (ACE) inhibitors, ASA, SAMe break down products such as methionine, MTA and folate, cardioprotectants, vasoprotectants, coagulation inhibitors.

Some embodiments of the present invention relate to combinations of SAMe with one or more active ingredients that are commonly prescribed or used for treatment of and/or prophylaxis of a disorder induced in whole or in part by oxidative or free-radical damage including, but are not limited to, antioxidants such as Vitamin A, Vitamin C, Vitamin E, polyphenols, flavonoids, selenium, carotenoids.

Some embodiments of the present invention relate to combinations of SAMe with one or more active ingredients that are commonly prescribed or used for treatment of and/or prophylaxis of a disorder induced in whole or in part by damage to the central nervous system such as brain injury or spinal cord injury including, but not limited to, neuroprotectants, nootropic agents, CNS modulators, analgesics, muscle relaxants, apoptosis inhibitors, bone modulators, antioxidants.

Some embodiments of the present invention relate to combinations of SAMe with methionine, MTA, folate, vitamin B6 and/or B12 as they are each correlated with lowering homocysteine production. Therefore, it is considered that combining SAMe with methionine, MTA, folate, methyl folate, vitamin B6 and/or B12 may result in increased supplementation of SAMe by enhancing the body's natural ability to make SAMe while at the same time supplementing SAMe with exogenous SAMe exhibiting an improved pharmacokinetic profile.

In some embodiments, an exemplary improved pharmacokinetic SAMe dosage form according to the invention may be included in a kit with a separate dosage form containing at least one other active ingredient, exemplified by one or more compounds suitable for the treatment of or commonly prescribed or used for the treating and/or prophylaxis in a subject a disease or disorder selected from the group consisting of, but not limited to, a mental or psychiatric disorder (e.g. psychotic or non-psychotic mental disorders such as depression and substance abuse disorders, respectively), a nervous system disease/disorder (e.g. a central nervous system disease such as Alzheimer's), other neurological disease/disorders (e.g. headaches and sleep disorders), conditions associated with injury to the central nervous system, a liver disease/disorder (e.g. alcoholic liver disease), a cancer (e.g. solid and blood-borne cancers), a joint disease/disorder (e.g. arthritis), an inflammatory disease/disorder (e.g. ulcerative colitis), an autoimmune disease/disorder (e.g. systemic lupus erythematosis and rheumatoid arthritis), a degenerative disease/disorder (e.g. Amyotrophic Lateral Sclerosis), a soft-tissue disease/disorder (e.g. a fibromyalgia disorder), a pain disease/disorder, a genetic disorder related to hyper or hypo methylation, a gastrointestinal disease/disorder, a cardiovascular disease/disorder, and a disorder induced in whole or in part by oxidative or free-radical damage, comprising administering to said subject an exemplary composition of the present invention which improves the pharmacokinetic profile of a physiologically effective amount of exogenous SAMe.

In some embodiments, an exemplary improved pharmacokinetic SAMe dosage form according to the invention may be included in a kit with a separate diagnostic agent or tool exemplified by one or more agents/tools suitable for use as part of a diagnostic test. In certain embodiments the diagnostic agent or tool is used as part of a test for measuring the levels of one or more biomarkers.

In addition to combinations of SAMe with the one or more additional ingredients exemplified above or methionine, MTA, folate, vitamin B6 and/or B12, administration of the exemplary improved pharmacokinetic SAMe formulations of the invention may also augment the effects of other drugs or nutritional supplements being taken by the subject. Thus, some exemplary embodiments of the present invention relate to combinations of SAMe with drugs or nutritional compounds already employed for treating other diseases for increasing the activity of said drugs or nutritional compounds.

The present invention is further described by the following examples. These examples, while illustrating certain specific aspects of the invention, should not be considered to limit or circumscribe the scope of the disclosed invention.

EXAMPLES

Example 1

SAMe Formulations of the Invention Generate $C_{max}$ Values Significantly Greater than Those from Commercially Available SAMe In order to identify and optimize processing components, methods and parameters that impart product characteristics which result in improved pharmacokinetic profiles, SAMe formulations comprising various excipients and prepared with certain final dosage form characteristics were compared with a commercially available SAMe formulation. In this example, a commercially available S-adenosyl methionine tosylate disulfate formulation was utilized as the control SAMe dosage form.

SAMe formulations of the invention were generated using standard procedures for making tablets and comprise the following:

| Ingredient (MSI-43) | % (w/w) |
|---|---|
| SAMe Disulfate Tosylate | 76.8 |
| Microcrystalline Cellulose 113 | 7.6 |
| Microcrystalline Cellulose 112 | 9.1 |
| Disintegrant | 5 |
| Colloidal Silicon Dioxide | 0.5 |
| Magnesium Stearate | 1.0 |

In order to improve the compressibility of SAMe, a dry granulation procedure ("slugging") was employed. The above ingredients were mixed and pressed through a mesh screen. Slugs were made on a Manesty SP press fitted with 16/32 tooling to a hardness of 2-4 kPa. Slugs were then milled on an Erweka Dry Granulator and pressed through a mesh screen. The final mixture was then compressed to a hardness of 12-17 kPa on a Stokes DS3 semi automatic press using an elongated oval die. Humidity was maintained at below 30% and temperature was maintained at 20-25° C. during the entire manufacturing process. The granules demonstrated good flow properties and no sticking or picking during compression.

Prior to applying an enteric coating to these tablets, a seal coat was first applied in order to improve the tablet surface properties. A stirred 12% suspension of a commercially available seal coat in purified water was applied to the uncoated SAMe tablets in an Aeromatic Coating Column using 55° C. inlet air temperature and 4-6 g/min spray rate until 2% weight gain was achieved.

A plasticized 80% solid (w/w) commercially available enteric coat designed to dissolve at pH 5.5 was then applied to the tablet formulations such that they would remain intact within the stomach. The enteric coating was generated using a stirred 30% aqueous suspension (56% of final coating suspension by weight), plasticizer 20% aqueous suspension (7% of final coating suspension by weight), triethyl citrate (2% of final coating suspension by weight) and purified water (35% of final coating suspension by weight). These components were mixed and then applied to the seal coated SAMe tablets in an Aeromatic Coating Column using 55° C. inlet air temperature and 4-6 g/min spray rate.

The manufacturing process produced dosage form characteristics which when combined with the specific combinations of SAMe and excipients gave rise to the exemplary SAMe formulation of the invention. Tablets were examined based on several in vitro test criteria including the following:
  Hardness: average range of 16 with variance (SDEV squared) of 3
  Average weight of tablets: 1100 mg (target 400 mg SAMe ion with standard pharmaceutical variance)
  Average size: 9.2 mm×19.1 mm
  Exterior Coating thickness: 6.4% weight gain
  Water Content: 2.2% w/w Once the final tablets of the invention were generated and characterized, they were administered to healthy volunteers in order to compare their in vivo pharmacokinetic profiles to those of a commercially available and routinely used SAMe tosylate disulfate formulation.

For the control group, seven healthy, male volunteers who had fasted were given a single dose of 1600 mg of the commercially available S-adenosyl methionine tosylate disulfate formulation. Similarly, for the test group, nine healthy and fasted male volunteers were administered 1600 mg of the SAMe formulation of the invention ("MSI-43") given as a single dose. The resulting pharmacokinetic profiles were studied by measuring the presence of SAMe in plasma at various time points after administration.

The graph in FIG. 1 shows the average SAMe plasma concentration curves for the aforementioned subjects each of whom received either a single 1600 mg dose of the commercially available S-adenosyl methionine tosylate disulfate formulation or a single 1600 mg dose of the novel SAMe formulation of the invention, MSI-43. For the commercially available SAMe formulation, an average $C_{max}$ of about 900 ng/mL was reached within approximately 3-4 hours of administration. As can be seen in the graph, and what was particularly of note here was that subjects who received a single dose of the SAMe formulation of the invention recorded an average $C_{max}$ of approximately 4000 ng/mL within less than about 3 hours of administration. These results clearly show that SAMe formulations of the present invention provide a significant improvement to the pharmacokinetic profile of SAMe once administered and lead to increases in SAMe $C_{max}$ and AUC values never disclosed before in the prior art outside of injectable forms.

Example 2

Targeted Dissolution "Window" Results in Superior Pharmacokinetic Profiles In Vivo In this example, additional SAMe formulations were made, which had differing amounts of disintegrants, coating thickness, and were generated under various processing parameters in order to compare their in vivo performance and in vitro dissolution profiles. Each formulation comprised:

| Ingredient | % (w/w) |
|---|---|
| SAMe Disulfate Tosylate | 76.8 |
| Microcrystalline Cellulose 113 | 7.5-9 |
| Microcrystalline Cellulose 112 | 11-13.5 |
| Disintegrant | 0-10 |
| Colloidal Silicon Dioxide | 0.5 |
| Magnesium Stearate | 1.0 |

The disintegrants used were sodium starch glycolate, croscarmellose or crosprovidone. The percent of microcrystalline cellulose may vary according to the amount of disintegrant, such that the final % (w/w) of the formulation totals 100%. The tablets were manufactured according to the processes as described in Example 1. The in vitro attributes described in Examples 1 were also measured. In vivo human tests were conducted as per described in Example 1. The following table provides a summary of the tablet characteristics and corresponding pharmacokinetic attributes and focuses on those formulations which exhibit improved pharmacokinetic profiles:

TABLE 1

IN VIVO PROFILE OF VARIOUS SAMe FORMULATIONS DOSED AT 1600 mg

| | T/C at tableting | RH/% at tableting | Enteric Coating Thickness by weight % | Average hardness/kP | Dissolution at 30 min post 6.8 pH | Average Cmax* (ng/mL of SAMe) | Tmax** (hrs) | $AUC_{0-t}$^^^ (h * ng/mL of SAMe) |
|---|---|---|---|---|---|---|---|---|
| MSI-03 | 17 | 32 | 8.0 | n/a | 5 | 401 | 3 | 4361 |
| MSI-09 | 24 | 34 | 8.0 | 12 | 4 | 1158 | 4 | 6929 |
| Commercial | n/a | n/a | n/a | 34.1 | 10 | 765 | 5 | 5261 |
| Commercial | n/a | n/a | n/a | 34.1 | 10 | 941 | 5 | 4504 |
| MSI-72 | 25 | 23 | 2.9 | 15.2 | 96 | 2067 | 3 | 10365 |
| MSI-90 | 32 | 28 | 3.6 | 15.4 | 86 | 2561 | 4 | 14013 |
| MSI-104 | 33 | 2 | 3.7 | 15.0 | 78 | 1846 | 3 | 10440 |
| MSI-111 | 29 | 15 | 3.6 | 17.4 | 94 | 3223 | 5 | 13402 |

*Average Cmax was calculated by averaging all subjects at each time point and then taking the maximum of the averages
**Tmax is the time point where Cmax* was determined
^^^AUC is area under the curve

Example 2a

Targeted Dissolution with Different Excipients

In this example, additional SAMe formulations are made, which have differing amounts of disintegrants and coating thickness, and different lubricants. The formulations are generated under various processing parameters in order to compare their in vivo performance and in vitro dissolution profiles. Each formulation comprised:

| Ingredient | % (w/w) |
|---|---|
| SAMe Disulfate Tosylate | 60-80% |
| Microcrystalline Cellulose 113 | 7-10 |
| Microcrystalline Cellulose 112 | 10-15 |
| Disintegrant | 0-10 |
| Colloidal Silicon Dioxide | 0-1 |
| Lubricant | 0.1-2 |

The disintegrants used may be sodium starch glycolate, croscarmellose, crospovidone or some other suitable disintegrant. The percent of microcrystalline cellulose may vary according to the amount of disintegrant, such that the final % (w/w) of the formulation totals 100%.

The tablets are manufactured according to the processes as described in Examples 1 and 2. The in vitro attributes described in Examples 1 are also measured. In vivo human tests are conducted as per described in Examples 1 and 2. The following table provides a summary of the lubricants that may be employed in the tablets according to the invention:

| Exemplary Lubricants |
|---|
| Calcium stearate |
| Stearic acid |
| Sodium benzoate |
| Leucine |
| Sodium stearyl fumarate |
| Talc |

Example 3

In Vitro Dissolution Profiles as a Predictor of In Vivo Performance

Dissolution profiles are routinely used as an in vitro marker to confirm final product and/or tablet characteristics. This profiling is typically performed according to USP standards and under conditions which mimic physiological pH (pH 6.8).

Figure 2A:
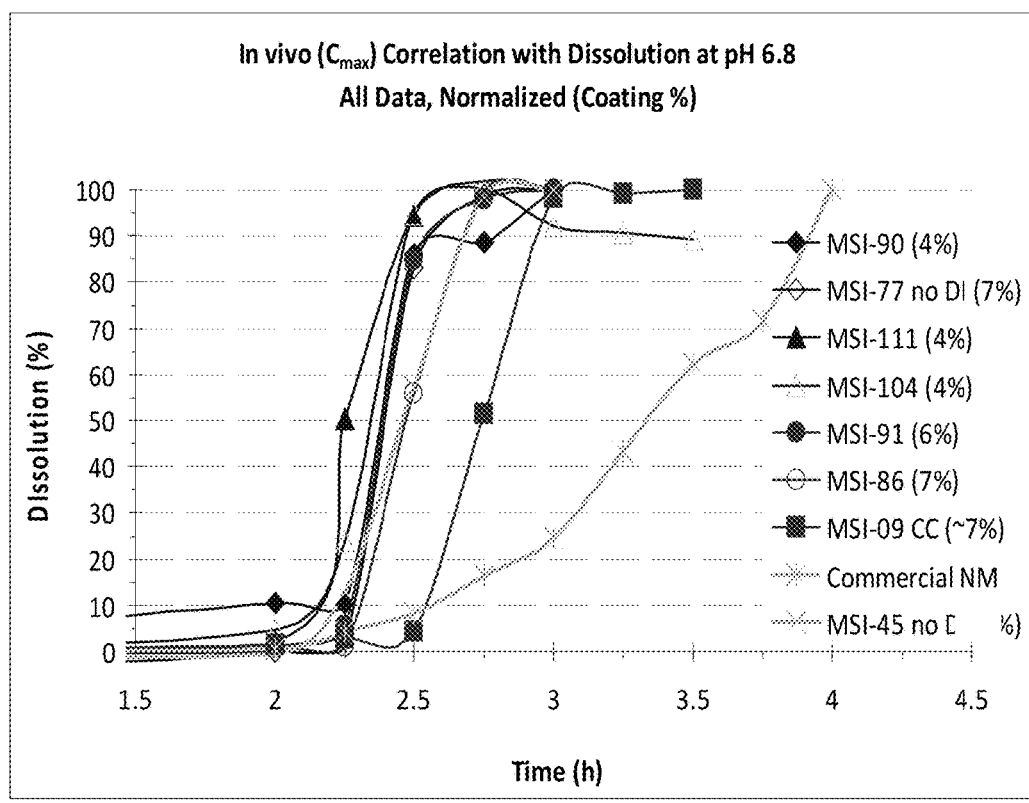
FIG. 2A is a graph of the dissolution profiles of various SAMe tablet formulations of the invention at pH 6.8 represented as the percent drug released over time (hours); and, FIG. 2B is a graph of the pH 6.0 dissolution profiles of the same SAMe tablet formulations of the invention as seen in FIG. 2A represented as the percent drug released over time (hours)

The dissolution test method used is typically as follows:
USP Apparatus II operated at 100 RPM
Fluid Phase: 1 L USP Simulated Gastric Fluid without enzyme, pH 1.2, 37° C.
Aqueous Buffer Phase—1 L USP simulated Intestinal Fluid without enzyme, pH 6.8, 37° C.
Tablets are exposed to the acid phase for two hours then transferred to the Buffer Phase
Aliquots are drawn following exposure to the acid phase for 2 hours, then at prescribed intervals while in the buffer phase
Samples are diluted 1→10 with n/10 HCL
Drug concentration is determined spectrophotometrically at 258 mm Eight different SAMe formulations were compared against the same commercially available SAMe product as mentioned previously and the dissolution profiles obtained are represented in FIG. 2A. As shown in the graph, the eight SAMe formulations of the invention all show rapid dissolution within 30 minutes of incubation in the aqueous buffer phase in comparison to the Commercially available SAMe (note this is between 2 and 2.5 hours on the X-axis as all samples are exposed to the acid phase for 2 hours prior to transfer and analysis in the buffer phase). Furthermore, the dissolution profiles of the eight SAMe formulations of the invention overlap such that it is difficult to differentiate between these formulations and all appear to be equally "rapid".

The SAMe formulations of the invention are coated with an enteric coating designed to dissolve in the region exiting the stomach and therefore the present investigators designed a new profiling method which would better mimic the conditions of the small intestine. Using this method, the buffer phase was adjusted to pH 6.0 rather than 6.8.

Figure 2B:
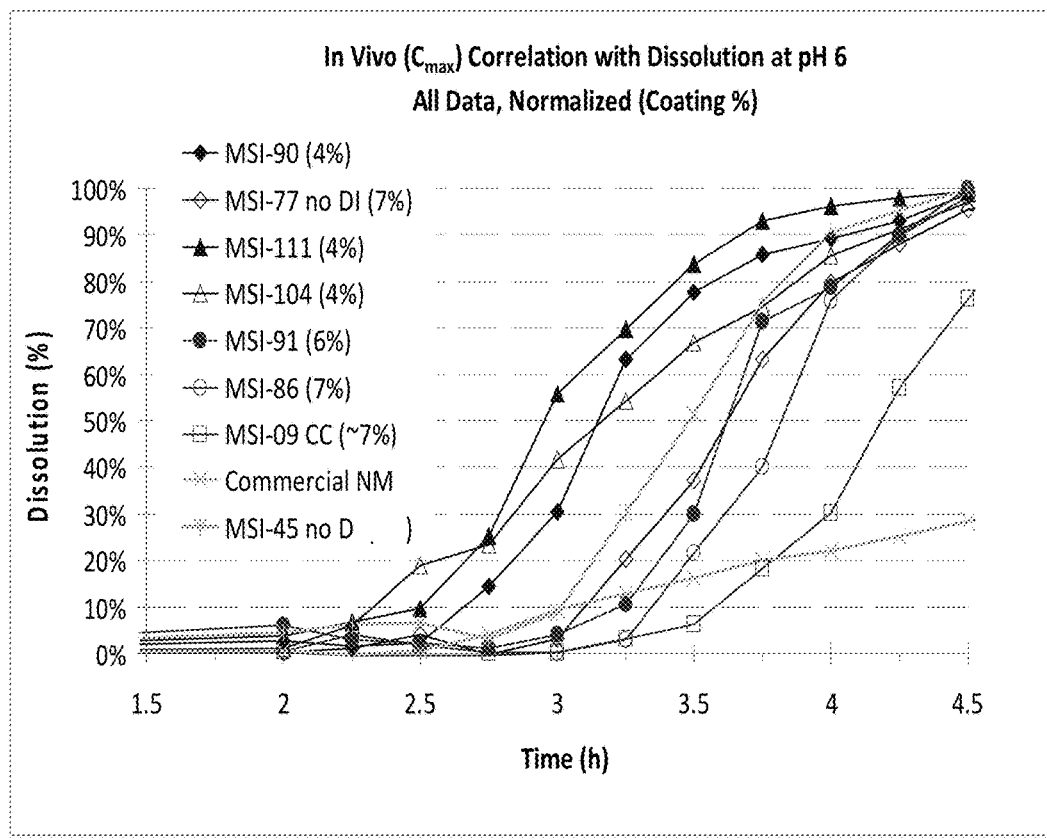

Surprisingly, the in vitro dissolution profiles generated under these conditions identified a clear distinction between the eight formulations of the invention as those that are either faster or slower to release drug in the earliest time points. The graph in FIG. 2B shows these profiles and clearly depicts MSI-111, MSI-90 and MSI-104 as 'fast-release' formulations. As seen in the table in Example 2 above, in vivo profiling of all of these formulations shows that these fast-release formulations have very high $C_{max}$ and AUC values and represent those formulations of the invention which exhibit improved pharmacokinetic profiles of SAMe.

Figure 3:
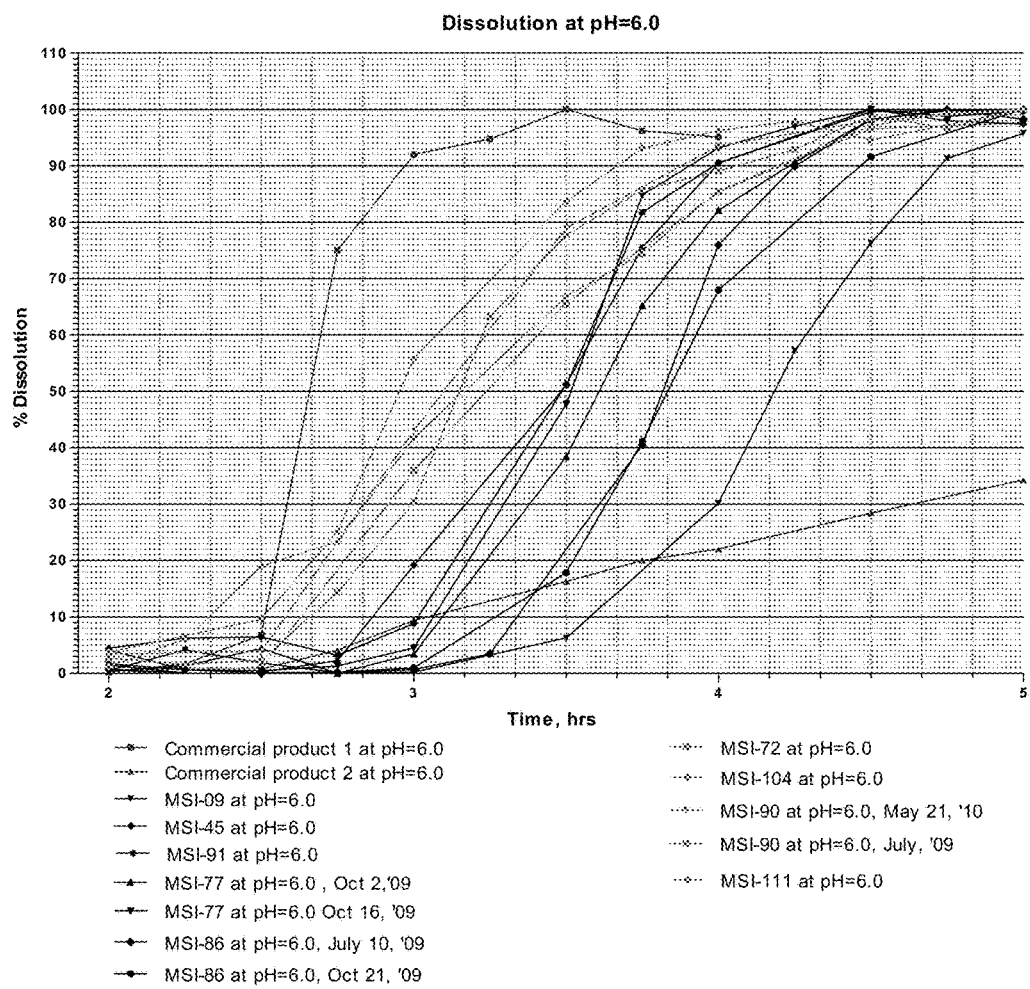
FIG. 3 is a graph of the pH 6.0 dissolution profiles of additional SAMe formulations of the invention in comparison to two commercially available SAMe tablets.

Also, when a commercially available rapid-dissolve SAMe product, "Commercial product 1", was compared against various formulations of the invention it was discovered that this extremely fast-dissolving formulation did not exhibit the very high in vivo SAMe $C_{max}$ and/or AUC values as exemplified and claimed in the present invention. Similarly, dissolution profiling of another commercially available SAMe product ("Commercial product 2"), which was utilized in the Examples above as well as the following Examples, showed that at pH 6.0 the dissolution of this product was "slow" in comparison to the improved PK SAMe formulations of the invention (a summary of these dissolution profiles is seen in FIG. 3). Therefore, surprisingly, there exists a "window" of dissolution that is neither too fast nor too slow and leads to unexpectedly high levels of SAMe in the plasma. Provided herein is thus a novel in vitro method for identifying SAMe formulations which exhibit improved pharmacokinetic profiles in vivo.

Example 4

Effect of Coating Thickness, Temperature and Relative Humidity on SAMe Pharmacokinetic Parameters The in vivo profiles of multiple SAMe formulations of the invention comprising different excipients and/or dosage form characteristics were compared. As seen in Table 2 below, the 'thin-coated' formulations generated high $C_{max}$ and AUC values. "Thin" coatings are meant to include those that are less than about 6% but more preferably targeted to about 4%. As seen in the table, relative humidity was maintained below 30%. It was necessary to maintain this low humidity in order to generate workable "thin" coated formulations. Temperature was maintained at less than 35° C.

TABLE 2

IN VIVO PROFILE (ranked by individual's averages) dose 1600 mg SAMe ion

| | T/C at tableting | RH/ % at tableting | average weight/g | Enteric Coating Thickness - targeted by weight % | average hardness/ kP | Dissolution at 0.5 hrs post 6.8 pH | Cmax* (ng/mL of SAMe) | Tmax** (hrs) | AUC 0-t^^^ (h * ng/ mL of SAMe) |
|---|---|---|---|---|---|---|---|---|---|
| Humidity between 15-35% and "thin" coatings: | | | | | | | | | |
| MSI-111 | 29 | 15 | 1.1 | 3.6 | 14.0 | 94 (84 at 1.5 hrs post pH 6.0) | 3223 | 6 | 13402 |
| MSI-90 | 32 | 28 | 1.1 | 3.6 | 15.0 | 86 (78 at 1.5 hrs post pH 6.0) | 2561 | 4 | 14013 |
| MSI-72 | 25 | 23 | 1.1 | 2.9 | 15.2 | 96 | 2067 | 3 | 10365 |
| Humidity at or below 10%: | | | | | | | | | |
| MSI-43 | 22 | 4 | 1.1 | 6.4 | 16.0 | 70 | 4017 | 3 | 13168 |
| MSI-77 | 22 | 0.6 | 1.1 | 6.5 | 17.4 | 83 | 2635 | 5 | 13927 |
| MSI-78 | 22 | 4 | 1.1 | 6.7 | 16.0 | 78 | 2299 | 4 | 13642 |
| MSI-79 | 22 | 4 | 1.1 | 6.9 | 15.4 | 54 | 2113 | 4 | 10250 |
| MSI-104 | 33 | 2 | 1.1 | 3.7 | 15.0 | 95 (67 at 1.5 hrs post pH 6.0) | 1846 | 3 | 10440 |
| MSI-105 | 33 | 2 | 1.1 | 5.9 | 15.0 | 78 | 2190 | 3 | 9994 |

*Average Cmax was calculated by averaging all subjects at each time point and then taking the maximum of the averages

**Tmax is the time point where Cmax* was determined

^^^AUC is area under the curve

When the functional (or enteric) coating thickness is reduced to around 4%, improved PK SAMe formulations of the invention are generated under conditions where the humidity levels can be as high as 35%. However, surprisingly, the present investigators also discovered that improved PK SAMe formulations of the invention generated under very low humidity conditions (less than or equal to 10%) are less sensitive to the thickness of the outer coating and improved PK SAMe formulations of the invention can be generated with functional coatings as thick as 9-10%. Therefore, the invention also relates to a method for making SAMe formulations with improved PK parameters by manufacturing said formulations under conditions wherein the relative humidity is about 10% or less.

Figure 4:
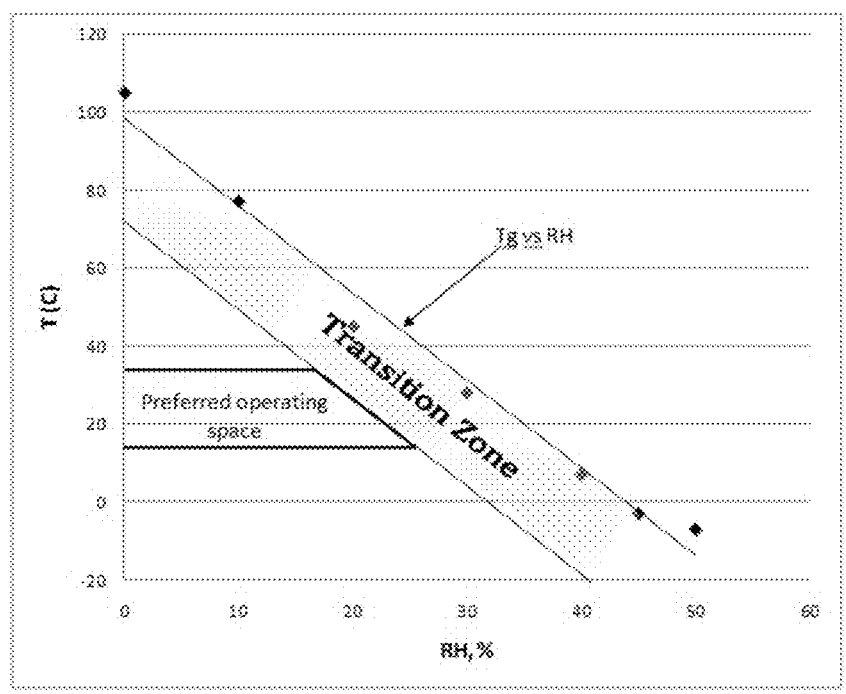
FIG. 4 is a graph showing the glass transition temperature (Tg) of SAMe as a function of relative humidity (RH).

The graph in FIG. 4 shows the effect of relative humidity and temperature on the glass transition temperature (Tg) of SAMe. As seen in the graph, there is a preferred operating range of these process parameters when preparing SAMe formulations of the invention in order to yield a Tg greater than room temperature. The lowest humidity (under 10%) is more preferable for those formulations where the coating thickness remains above about 4%.

Example 5

SAMe Formulations of the Invention Result in a Reduced Effective Dose

SAMe formulations of the invention comprising different excipients and/or dosage form characteristics were compared with a commercially available SAMe formulation at both comparative doses as well as at half the dose. In this example, the same commercially available S-adenosyl methionine tosylate disulfate formulation stated before was utilized as the control SAMe dosage form.

A first SAMe formulation of the invention (termed, "MSI-72") comprising sodium starch glycolate (SSG), colloidal silicon dioxide and magnesium stearate was generated using similar excipients and procedures as described in Example 1. The specific MSI-72 formulation was as follows:

| Ingredient | % (w/w) |
| --- | --- |
| SAMe Disulfate Tosylate | 76.8 |
| Microcrystalline Cellulose 113 | 7.6 |
| Microcrystalline Cellulose 112 | 9.1 |
| Sodium Starch Glycolate | 5 |
| Colloidal Silicon Dioxide | 0.5 |
| Magnesium Stearate | 1.0 |

As detailed in Example 1, the same seal coat followed by an enteric coating designed to dissolve at pH 5.5 was applied to the tablets.

For comparison of the above MSI-72 SAMe formulation of the invention with a commercially available SAMe formulation, a single 1600 mg dose of either the commercially available S-adenosyl methionine tosylate disulfate formulation or the MSI-72 SAMe formulation was given to two groups of healthy and fasted, male volunteers (seven in each group). A single dose of 800 mg of the proprietary SAMe formulation was also compared in a third study group to the same 1600 mg dose of the commercially available SAMe. The resulting pharmacokinetic profiles were studied by measuring the presence of SAMe in plasma at various time points after administration.

Figure 5A:
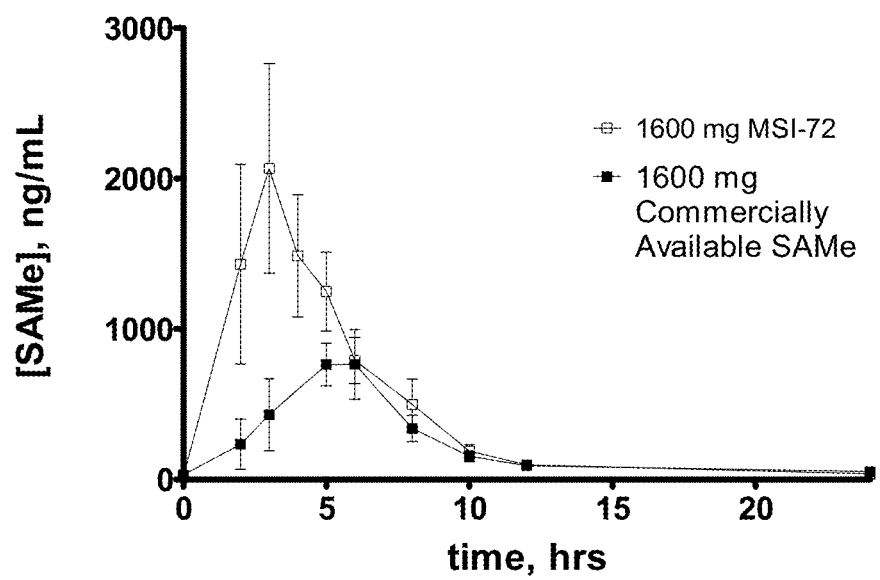
FIG. 5A is a graph of the average SAMe plasma concentration with the standard error of the mean and showing the average maximum plasma concentration ($C_{max}$) from seven subjects who were administered either a 1600 mg (SAMe ion) oral dose of SAMe formulations of the invention (MSI-72; open squares) or a 1600 mg (SAMe ion) oral dose of a commercially available oral formulation of SAMe (closed squares); and, FIG. 5B is a graph of the average SAMe plasma concentration with the standard error of the mean and showing the maximum plasma concentration ($C_{max}$) from seven subjects who were administered either an 800 mg (SAMe ion) oral dose of the SAMe formulations of the invention reported in FIG. 5A (open squares) or a 1600 mg (SAMe ion) oral dose of the same commercially available oral formulation of SAMe also detailed in FIG. 5A (closed squares); and, FIG. 5C is a graph of the average SAMe plasma concentration with the standard error of the mean and showing the maximum plasma concentration ($C_{max}$) from seven subjects who were administered either an 800 mg (SAMe ion) oral dose of a different SAMe formulation of the invention, MSI-69 (open squares) or a 1600 mg (SAMe ion) oral dose of the same commercially available oral formulation of SAMe also detailed in FIG. 5A (closed squares)

The graph in FIG. 5A shows the average plasma SAMe concentration curve for seven subjects who received a single 1600 mg dose of the commercially available S-adenosyl methionine tosylate disulfate formulation in comparison to the average plasma SAMe concentration curve for seven subjects who received 1600 mg of the SAMe formulation of the present invention (MSI-72) given as a single dose. As can be seen in the graph, the average $C_{max}$ for the proprietary SAMe formulation is significantly increased in comparison to conventional SAMe therapy.

Figure 5B:
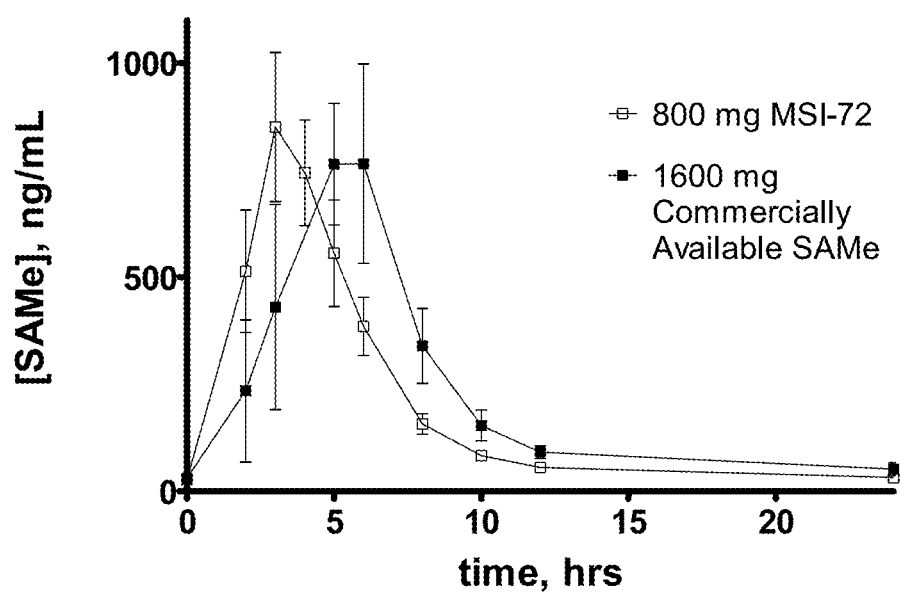

Moreover, the data presented in FIG. 5B represent the same 1600 mg dose of conventional, commercially available SAMe therapy as detailed above; however the MSI-72 SAMe formulation was dosed at only half of the dose. 800 mg of MSI-72 was administered as a single dose to seven healthy and fasted, male volunteers and the presence of SAMe in plasma was measured after administration at the indicated time points. As can be seen in the graph, the average $C_{max}$ of the inventive formulation when using only half the dose is comparable to the full, 1600 mg dose of the commercially available SAMe formulation.

Another SAMe formulation of the invention (termed, "MSI-69") comprising microcrystalline cellulose, croscarmellose, colloidal silicon dioxide and magnesium stearate was also generated using similar procedures as described in Example 1. This formulation was directly compared at half of the dose (800 mg) to a 1600 mg dose of the commercially available S-adenosyl methionine tosylate disulfate formulation mentioned above. Seven healthy and fasted male volunteers were administered a single 800 mg dose of MSI-69 and the presence of SAMe in plasma was measured after administration at the indicated time points.

Figure 5C:
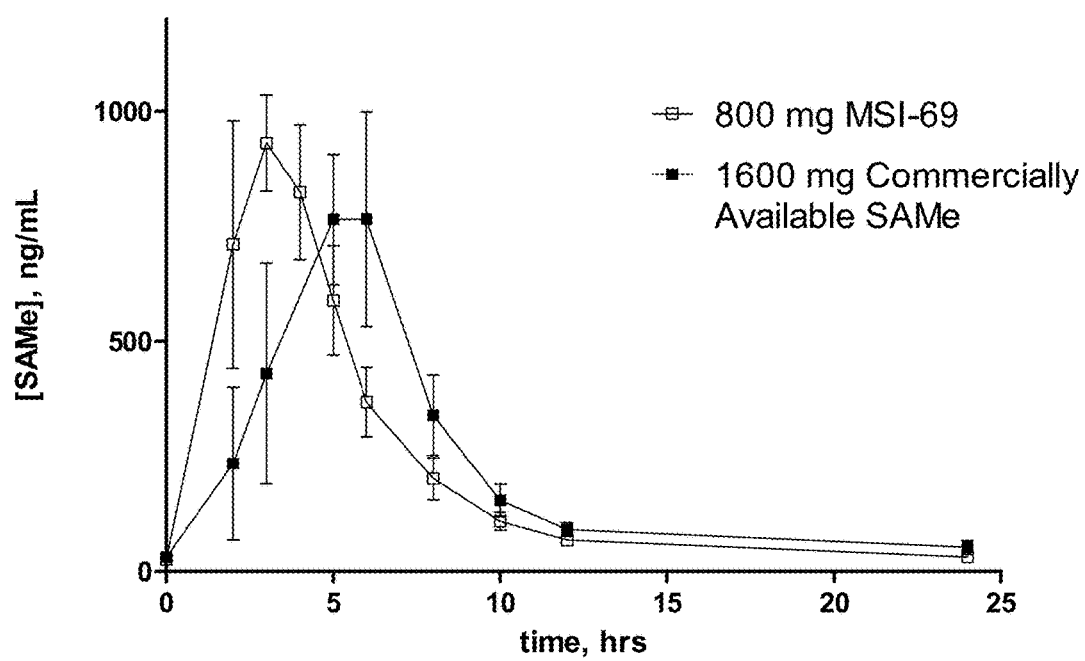

As seen in the graph in FIG. 5C, the average $C_{max}$ of the second inventive formulation (MSI-69) when using only half the dose is also comparable to the full, 1600 mg dose of the commercially available SAMe formulation.

These results clearly show that the SAMe formulations of the invention provide a significantly reduced effective dose and thus improved pharmacokinetic profile in comparison to approximately double the dose of the commercially available SAMe dosage forms used here.

A summary of the AUC and Cmax values obtained from dosing SAMe at 800 mg using either MSI-69 or MSI-72 as described above as well as two different MSI formulations (MSI-90 and MSI-105) is shown in Table 4 below in comparison to two commercially available SAMe products.

The compositions of the invention provide significantly higher exposure in comparison to the two commercially available SAMe products as measured by $C_{max}$ and in particular, AUC at the 800 mg dose.

TABLE 4

Pharmacokinetic Analysis of 800 mg SAMe Doses

| Test Article | Dose | AUC (ng · h/mL) 0-24 hours | Cmax[1] (ng/mL) |
| --- | --- | --- | --- |
| Commercial SAMe #1 | 800 mg, BID (t = 0, and 8 hrs) | 3572[2] | 784 |
| Commercial SAMe #2 | 800 mg, QD | 3311 | 595 |
| MSI-69 | 800 mg, QD | 5279 | 931 |
| MSI-72 | 800 mg, QD | 4590 | 851 |
| MSI-90 | 800 mg, QD | 5301 | 865 |
| MSI-105 | 800 mg, QD | 6372 | 1106 |

[1]The Cmax values are derived by averaging the concentration of all subjects at each time point.
[2]The AUC determination for the Commercial SAMe product #1 was calculated by adjusting the SAMe plasma concentration for the 12 and 24 hour time point to the concentrations found in the pre-dose baseline level. This adjustment is necessary in order to remove the effects of the second dose which was administered at the 8 hour time point, and thus allow an AUC comparison to the other periods which were only given a single SAMe dose at t = 0.

Example 6

SAMe Formulations of the Invention Result in a Reduced Food Effect Profile

Once a day dosing using the presented formulations was compared against a simulated twice a day dosing of a routinely used commercially available SAMe product is provided. As mentioned previously, conventional SAMe formulations are typically dosed twice-daily (BID); and the second dose given late afternoon may contribute to insomnia and/or other sleep-related side effects (e.g. restlessness) because of a "food affect", since the second dose is not administered to a fasted stomach.

The amount and/or type of food present in the stomach or gastrointestinal tract of an individual can cause a delay in the time taken for an API within a tablet (or other dosage form) to be dissolved and absorbed into the blood stream. In BID dosing of SAMe, the second dose being administered to fed individuals is likely to delay the amount of time in which the second SAMe $C_{max}$ will be achieved (i.e. a delay in the second $T_{max}$). Therefore, the $C_{max}$ of the second dose (and potential stimulatory effects associated with this) would occur during normal sleep hours which may explain why insomnia and other sleep-related side effects are common with conventional SAMe treatments. Once a day dosing using SAMe formulations of the invention, which deliver the equivalent total daily amount of SAMe as with conventional bi-daily dosing, is likely to alleviate such side effects, particularly when administered in the early morning to fasted individuals, as only one $C_{max}$ will occur daily and during normal waking hours.

Figure 6:
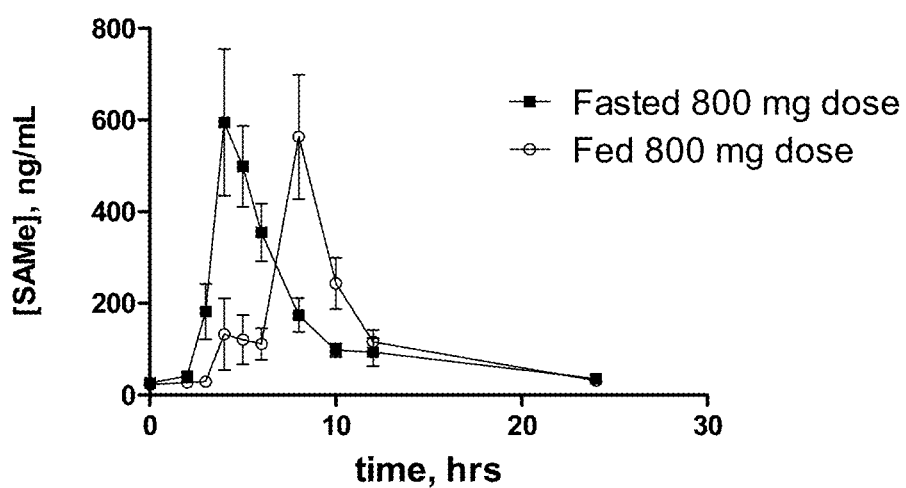
FIG. 6 is a graph of the average SAMe plasma concentration with the standard error of the mean and showing the pharmacokinetics of subjects given 800 mg (SAMe ion) of a commercially available oral formulation of S-adenosyl methionine tosylate disulphate wherein the subjects were either fed (open circles) or fasted (closed squares) prior to administration of the 800 mg dose.

FIG. 6 shows the "food affect" associated with a fed versus fasted administration of a commercially available SAMe tosylate disulfate formulation, dosed twice-daily at 800 mg. The strong food affect is seen in the delay of $T_{max}$ of the "fed" dosing to post 8 hours after administration of the single, 800 mg dose. This is in contrast to an average $T_{max}$ of approximately four hours observed under fasted conditions. Clearly the presence of ingested food in the "fed" subjects causes a significant delay in the time taken to reach the $C_{max}$.

Figure 7:
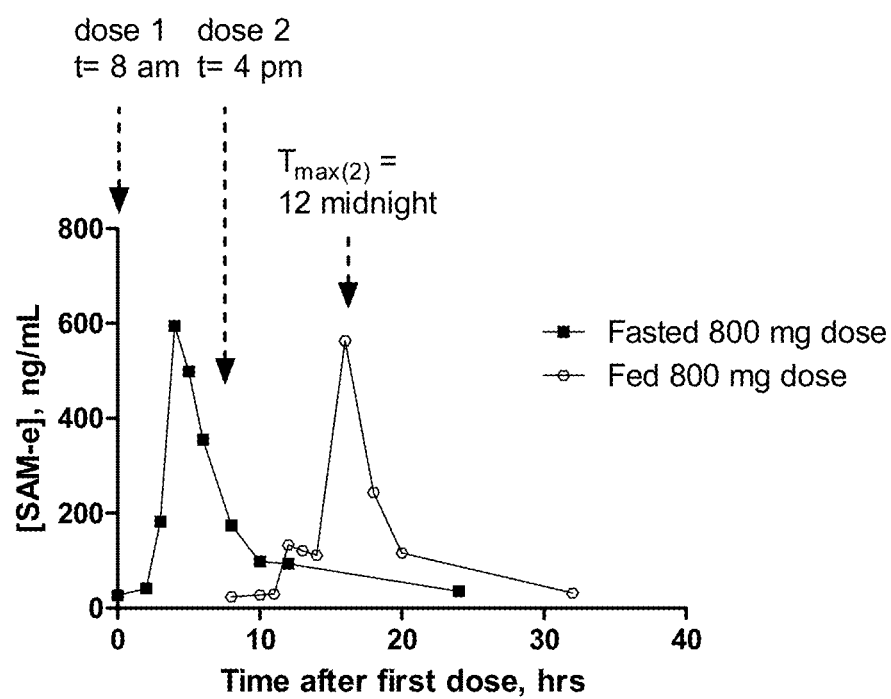
FIG. 7 is a graph with two pharmacokinetic profiles, both of the average SAMe plasma concentration. This graph, based on the data shown in FIG. 6, is a simulation of an 800 mg BID (twice daily) dosing separated by 8 hours. The subjects were dosed with 800 mg (SAMe ion) of a commercially available oral formulation of S-adenosylmethionine disulfate tosylate under fasted (closed squares) or fed (open circles) conditions. 8 hours was added to each of the time points for the fed dataset to simulate a 4:00 pm dosing.

FIG. 7 represents a simulation of a 1600 mg bi-daily (BID) dosing of the commercially available product given at time 0 hours fasted (8:00 am) and time 8 hours non-fasted or "fed" (4:00 pm). As seen in the graph, the first $T_{max}$ is achieved within approximately 3-4 hours of the first dose given when the individuals had fasted. However, the second $T_{max}$, from the second dose given to "fed" individuals takes about 8 hours to occur. The extended delay in $T_{max}$ experienced in the second dose under non-fasted conditions results in the $C_{max}$ being reached between 15 and 18 hours after the first dose and correlates to between 11:00 pm to 2:00 am. This implies that the second dose is producing a SAMe $C_{max}$ during normal sleep times, which may explain the presence of insomnia and other sleep-related side effects associated with current regimented BID dosing of SAMe.

Through the formulations exemplified in the present invention, once a day dosing has been shown to provide equivalent or higher SAMe AUCs with reduced $T_{max}$ variability and a lack of high SAMe levels during normal night sleeping times. The improved pharmacokinetic profile of these formulations with once a day dosing should result in reduced side effect profiles associated with SAMe administration.

A comparison of the simulated, conventional twice a day dosing regimen to the formulations embodied in the present invention are shown below in Table 4:

TABLE 4

IN VIVO PROFILE (ranked by individual's averages)

| | dose of SAMe ion | *Cmax (ng/mL of SAMe) | **Tmax (hrs) | ***AUC (ng h/mL of SAMe) |
|---|---|---|---|---|
| Simulated 1600 mg BID commercial product | 2 × 800 mg | 714 & 630 | 4 & 16 | 6445* |
| MSI-79 | 1600 mg | 2567 | 4 | 10250 |
| MSI-72 | 1600 mg | 2646 | 4 | 10365 |
| MSI-78 | 1600 mg | 3490 | 4 | 13642 |
| MSI-77 | 1600 mg | 3965 | 5 | 13927 |
| MSI-43 | 1600 mg | 4488 | 4 | 13168 |

1600 mg dose was given to subjects in one dose at 8 am after an overnight fast
*Average Cmax was calculated by averaging individual's Cmax values (no outliers)
**Tmax is the time point where *Cmax was determined
***AUC is area under the curve (AUC calculated for simulated dose by adding fed and fasted dosing profiles together)

What is claimed is:

1. An S-adenosylmethionine (SAMe) composition formulated for oral administration comprising 60-80% SAMe, 0-10% disintegrant, 0-1% colloidal silicon dioxide, 0.1-2% lubricant, and at least 7% of a binder, wherein all % values are based on the percentage by weight of the composition, and wherein oral administration of said composition to a selected subject group produces in said selected subject group: (a) an average maximum SAMe blood plasma concentration (average $C_{max}$) of at least about 110 ng/mL per each 100 mg of SAMe ion in said composition; and (b) an average SAMe plasma area under curve (average AUC) within a range of about 400 ng·h/mL to about 800 ng·h/mL per each 100 mg of SAMe ion in said composition.

2. The composition of claim 1, wherein said disintegrant is selected from sodium starch glycolate, croscarmellose sodium, crosprovidone, and combinations thereof.

3. The composition of claim 1, wherein said lubricant is selected from magnesium stearate, talc, calcium stearate, stearic acid, stearin hydrogenated vegetable oils, sodium benzoate, leucine, sodium stearyl fumarate, and combinations thereof.

4. The composition of claim 1, wherein said binder is selected from a sugar, gelatin, a gum, microcrystalline cellulose, waxes, synthetic polymers, polyethylene glycol, polyvinyl pyrrolidone, and combinations thereof.

5. The composition of claim 1, wherein the composition comprises one of tablets, pastes, capsules, granules, caplets, and lozenges.

6. The composition of claim 5, wherein said composition comprises a functional coating.

7. The composition of claim 6, wherein said functional coating is an enteric coating.

8. The composition of claim 1, wherein the composition when administered to a selected subject group provides in said selected subject group an average Tmax and/or Cmax with reduced variation.

9. The composition of claim 1, wherein the composition when administered to a selected subject group provides in said selected subject group an improved pharmacokinetic profile through: an equivalent average AUC to bi-daily dosing and/or reduced side effects through once a day dosing.

10. The composition of claim 1, wherein oral administration of said composition to a selected subject group produces in said selected subject group an average $C_{max}$ of at least about 120 ng/mL per each 100 mg of SAMe ion in said composition.

11. The composition of claims 1, wherein the subject is human.

12. A method of treating a disease or disorder, comprising administering to a human subject in need of such treatment an effective amount of the composition of one of claim 1-4, 5-7, or 8-11.

13. A method for improving the pharmacokinetic parameters of exogenous SAMe administered to a subject, said method comprising administering to the subject a composition formulated for oral administration comprising 60-80% SAMe, 0-10% disintegrant, 0-1% colloidal silicon dioxide, 0.1-2% lubricant, and at least 7% of a binder, wherein all % values are based on the percentage by weight of the composition, and wherein oral administration of said composition to a selected subject group produces in said selected subject group: (a) an average maximum SAMe blood plasma concentration (average $C_{max}$) of at least about 110 ng/mL per each 100 mg of SAMe ion in said composition; and (b) an average SAMe plasma area under curve (average AUC) within a range of about 400 ng·h/mL to about 800 ng·h/mL per each 100 mg of SAMe ion in said composition.

14. The method of claim 13, wherein the composition is a nutraceutically acceptable composition.

15. An S-adenosylmethionine (SAMe) nutraceutically acceptable composition formulated for oral administration comprising 60-80% SAMe, 0-10% disintegrant, 0-1% colloidal silicon dioxide, 0.1-2% lubricant, and at least 7% of a binder, wherein all % values are based on the percentage by weight of the composition, and wherein oral administration of said composition to a selected subject group produces in said selected subject group: (a) an average maximum SAMe blood plasma concentration (average $C_{max}$) of at least about 110 ng/mL per each 100 mg of SAMe ion in said composition; and (b) an average SAMe plasma area under curve (average AUC) within the range of about 400 ng·h/mL to about 800 ng·h/mL per each 100 mg of SAMe ion in said composition.

* * * * *